(12) United States Patent
Charifson et al.

(10) Patent No.: US 7,727,992 B2
(45) Date of Patent: Jun. 1, 2010

(54) GYRASE INHIBITORS AND USES THEREOF

(75) Inventors: Paul S. Charifson, Framingham, MA (US); David D. Deininger, Arlington, MA (US); Joseph Drumm, Westborough, MA (US); Anne-Laure Grillot, Cambridge, MA (US); Yusheng Liao, Lexington, MA (US); Patricia Oliver-Shaffer, Acton, MA (US); Dean Stamos, Framingham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 881 days.

(21) Appl. No.: 10/459,420

(22) Filed: Jun. 11, 2003

(65) Prior Publication Data

US 2010/0105701 A1    Apr. 29, 2010

Related U.S. Application Data

(60) Provisional application No. 60/429,077, filed on Nov. 26, 2002, provisional application No. 60/388,665, filed on Jun. 13, 2002.

(51) Int. Cl.
| C07D 239/42 | (2006.01) |
| A61K 31/505 | (2006.01) |
| A61K 31/44 | (2006.01) |
| C07D 239/00 | (2006.01) |
| C07D 401/00 | (2006.01) |

(52) U.S. Cl. .................. 514/256; 514/269; 514/338; 544/242; 544/298; 546/273.4

(58) Field of Classification Search ................ 546/112, 546/273.4; 544/242, 298
See application file for complete search history.

(56) References Cited

U.S. PATENT DOCUMENTS

| 5,529,998 | A | 6/1996 | Häbich et al. |
| 5,643,935 | A | 7/1997 | Dykstra et al. |
| 6,632,809 | B2 * | 10/2003 | Grillot et al. ............... 514/215 |
| RE40,245 | E | 4/2008 | Grillot et al. |
| 7,414,046 | B2 * | 8/2008 | Grillot et al. ............... 514/215 |
| 2004/0043989 | A1 * | 3/2004 | Grillot et al. ........... 514/217.07 |
| 2004/0235886 | A1 | 11/2004 | Charifson et al. |
| 2005/0038247 | A1 | 2/2005 | Charifson et al. |
| 2005/0256136 | A1 | 11/2005 | Charifson et al. |
| 2006/0025424 | A1 | 2/2006 | Charifson et al. |

FOREIGN PATENT DOCUMENTS

| EP | 0 433 648 | 6/1991 |
| WO | WO 00/71522 | 11/2000 |
| WO | WO 02/060879 | 8/2002 |

OTHER PUBLICATIONS

Skopenko, V.V., et al., "Organotin Carbamoyldicyanomethanide, nitrosocarbamoylcyanomethanide, and carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).

* cited by examiner

Primary Examiner—Alton N Pryor
(74) Attorney, Agent, or Firm—Michael C. Badia

(57) ABSTRACT

The present invention relates to compounds which inhibit bacterial gyrase and pharmaceutically acceptable compositions comprising said compounds. These compounds, and compositions thereof, are useful in treating bacterial infection. Accordingly, the present invention also relates to methods for treating bacterial infections in mammals. The present invention also relates to a method for preparing these compounds.

2 Claims, No Drawings

GYRASE INHIBITORS AND USES THEREOF

CROSS REFERENCE TO RELATED APPLICATIONS

This application claims priority to U.S. Provisional Patent Application 60/388,665 filed Jun. 13, 2002 and U.S. Provisional Patent Application 60/429,077 filed Nov. 26, 2002, the contents of which are incorporated herein by reference.

FIELD OF THE INVENTION

The present invention is in the field of medicinal chemistry and relates to compounds, and pharmaceutical compositions thereof, that inhibit bacterial gyrase and/or Topo IV. The compounds are useful as inhibitors of bacterial gyrase and/or Topo IV activity. The present invention also relates to methods for treating bacterial infections in mammals and to methods for decreasing bacterial quantity in a biological sample.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960' s SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer magazine*, September, 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes which catalyze the interconversion of topological isomers of DNA (see generally, Kornberg and Baker, *DNA Replication*, 2d Ed., Chapter 12, 1992, W.H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely used, quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and trovafloxacin. These compounds bind to GyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective GyrB inhibitor that overcomes these drawbacks. Such an inhibitor would be an attractive antibiotic candidate, without a history of resistance problems that plague other classes of antibiotics.

Replication fork movement along circular DNA can generate topological changes both ahead of the replication complex as well as behind in the already replicated regions (Champoux, J. J., *Annu. Rev. Biochem.*, 2001, 70, 369-413). While DNA gyrase can introduce negative supercoils to compensate for the topological stresses ahead of the replication fork, some overwinding can diffuse back into the already replicated region of DNA resulting in precatenanes. If not removed, the presence of the precatenanes can result in interlinked (catenated) daughter molecules at the end of replication. TopoIV is responsible for separating the catenated daughter plasmids as well as removal of precatenanes formed during replication ultimately allowing for segregation of the daughter molecules into daughter cells. Topo IV is composed of two ParC and 2 parE subunits as a C2E2 tetramer (where the C and E monomers are homologuous to the A and B monomers of gyrase, respectively) that requires ATP hydrolysis (at the N-terminus of the E subunit) to reset the enzyme to re-enter the catalytic cycle. Topo IV is highly conserved among bacteria and is essential for bacterial replication (Drlica and Zhao, *Microbiol. Mol. Biol. Rev.*, 1997, 61, 377).

While less attention has been paid to inhibitors that target ParE of TopoIV, the action of the newer quinolones on the ParC region has been widely studied (Hooper, D. C., *Clin. Infect. Dis.*, 2000, 31(Suppl 2): S24-28). It has been demonstrated that moxifloxacin and gatifloxacin have more balanced activities against Gyrase and TopoIV resulting in expanded Gram positive coverage as well as lower levels of resistance caused primary-target mutation. In those cases, susceptibility is limited by the sensitivity of the second target to the antibacterial agent. Thus, agents that can effectively inhibit multiple essential targets can result in an expanded spectrum of potencies, improved antibacterial potencies, improved potency against single target mutants, and/or lower spontaneous rates of resistance.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

SUMMARY OF THE INVENTION

It has now been found that compounds of this invention, and pharmaceutically acceptable compositions thereof, are effective as inhibitors of gyrase and/or Topo IV. These compounds have the general formula I:

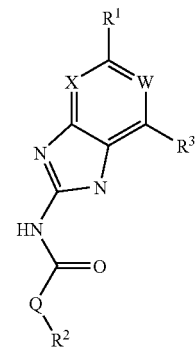

or a pharmaceutically acceptable salt thereof, wherein X, Q, W, $R^1$, $R^2$, and $R^3$ are as defined below.

These compounds, and pharmaceutically acceptable compositions thereof, are useful for treating or lessening the severity of bacterial infections. In particular, the compounds of the present invention are useful in treating or lessening the severity of urinary tract infections, pneumonia, prostatitis, skin and soft tissue infections, intra-abdominal infections, or infections of febrile neutropenic patients.

DESCRIPTION OF THE INVENTION

The present invention relates to a compound of formula I:

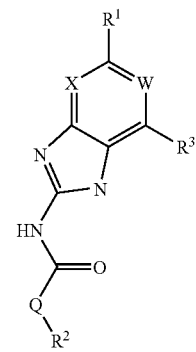

or a pharmaceutically acceptable salt thereof, wherein:
Q is —$CH_2$—, —NH— or —O—;
W is selected from nitrogen or C—$R^4$;
X is selected from CH or CF;
$R^1$ is a 5-6 membered aryl ring having 1-3 heteroatoms independently selected from oxygen, nitrogen, or sulfur, wherein:
  $R^1$ is substituted with 0-3 groups independently selected from R, oxo, $CO_2R'$, OR', N(R')$_2$, SR', $NO_2$, halogen, CN, C(O)N(R')$_2$, NR'C(O)R', $SO_2R'$, $SO_2N(R')_2$, or NR'$SO_2$R';
each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:
  R' is substituted with 0-3 groups independently selected from halogen, oxo, R°, N(R°)$_2$, OR°, $CO_2R°$, NR°C(O) R°, C(O)N(R°)$_2$, $SO_2R°$, $SO_2N(R°)_2$, or NR°$SO_2$R°;

each $R°$ is independently selected from hydrogen or $C_{1-4}$ aliphatic;

$R^2$ is selected from hydrogen or $C_{1-3}$ aliphatic group;

$R^3$ is selected from C(O)NHR, C(O)N(R)$_2$, CH(O), C(O)R, CO$_2$R, C(O)C(O)N(R$^2$)R, SO$_2$R, SO$_2$N(R)$_2$, SO$_2$NHR, C(R')=NOR, C(R')=NOH, C(R')=NR, C(R')=N—N(R$^2$)R, NO, or NO$_2$;

each R is independently selected from T-Ar or a $C_{1-6}$ aliphatic group, wherein:
  said $C_{1-6}$ aliphatic group is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R';

T is (CH$_2$)$_y$, wherein y is 0, 1, or 2;

Ar is selected from:
  (a) a 3-8 membered saturated, unsaturated, or aryl ring;
  (b) a 3-7 membered heterocyclic ring having 1-3 heteroatoms independently selected from nitrogen, oxygen, or sulfur; or
  (c) a 5-6 membered heteroaryl ring having 1-3 heteroatoms independently selected from nitrogen, oxygen, or sulfur, wherein:
    Ar is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R'; and $R^4$ is selected from hydrogen, fluorine, or OCH$_3$.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched $C_1$-$C_8$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "unsaturated", as used herein, means that a moiety has one or more units of unsaturation, and includes aryl rings.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

According to one embodiment, the present invention relates to a compound of formula I wherein Q is —NH—.

According to another embodiment, the present invention relates to a compound of formula I wherein Q is —O—.

According to another embodiment, the present invention relates to a compound of formula I wherein Q is —CH$_2$—.

Preferred $R^1$ groups of formula I are selected from an optionally substituted phenyl or 5-6 membered heteroaryl ring having 1-2 nitrogens. More preferred $R^1$ groups of formula I are selected from an optionally substituted pyrid-2-yl, pyrid-3-yl, pyrid-4-yl, pyrimidin-2-yl, pyrimidin-4-yl, pyrimidin-5-yl, imidazol-1-yl, imidazol-2-yl, imidazol-4-yl, or imidazol-5-yl ring. Most preferred $R^1$ groups of formula I are optionally substituted rings selected from pyrid-3-yl, pyrid-4-yl, pyrimidin-5-yl, or imidazol-1-yl.

According to another embodiment, $R^1$ is a pyridone ring. More preferably, $R^1$ is 4-pyridone.

Preferred substituents on the $R^1$ group of formula I, when present, are selected from halogen, oxo, R, $CO_2R'$, OR', $N(R')_2$, SR', $C(O)N(R')_2$, NR'C(O)R', $SO_2R'$, $SO_2N(R')_2$, or NR'$SO_2R'$. When $R^1$ is substituted with T-Ar, preferred substituents include those wherein Ar is an optionally substituted ring selected from a 5-6 membered heterocyclic ring having 1-3 heteroatoms independently selected from nitrogen, oxygen, or sulfur, or a 5-6 membered aryl ring having 0-3 heteroatoms independently selected from nitrogen, oxygen, or sulfur. More preferred substituents on the $R^1$ group of formula I, when present, are selected from oxo, fluoro, chloro, $N(CH_3)_2$, $NHCH_2CH_3$, NH-cyclopropyl, $NH_2$, NHC(O)$CH_3$, C(O)NHcyclopropyl, methyl, ethyl, t-butyl, isobutyl, cyclopropyl, isopropyl, $CH_2$phenyl, $CH_2$pyridin-2-yl, $CH_2$pyridin-3-yl, $CH_2$pyridin-4-yl, OH, $OCH_3$, $OCH_2CH_3$, $OCH_2$phenyl, $OCH_2$pyridin-3-yl, $CH_2$piperidinyl, $CH_2$cyclopropyl, or $CH_2CH_2OCH_3$.

When two substituents on adjacent positions of $R^1$ of formula I are taken together to form an optionally substituted ring fused to $R^1$. Preferred rings formed thereby are 5-6 membered saturated, partially unsaturated, or aryl rings having 0-2 heteroatoms independently selected from nitrogen, oxygen, or sulfur. More preferred rings fused to $R^1$ are selected from a 5-membered saturated ring having two oxygens or a 6-membered saturated ring having two oxygens. Preferred substituents on said ring fused to $R^1$ are halogen and more preferably fluorine.

Preferred $R^2$ groups of formula I are selected from methyl, ethyl, isopropyl, or cyclopropyl. More preferred $R^2$ groups of formula I are methyl, cyclopropyl, or ethyl. Most preferably, $R^2$ of formula I is ethyl.

Preferred $R^3$ groups of formula I are selected from C(O)NHR, C(O)R, C(R)=NOR, C(R)=NOH, or $CO_2R$, wherein:
each R is independently selected from an optionally substituted $C_{1-4}$ group or T-Ar, wherein:
T is $(CH_2)_y$, wherein y is 0, 1, or 2; and
Ar is an optionally substituted ring selected from a 5-6 membered saturated, unsaturated or aryl ring, a 5-6 membered heterocyclic ring having 1-2 heteroatoms independently selected from nitrogen, oxygen, or sulfur, or a 5-6 membered heteroaryl ring having 1-2 heteroatoms independently selected from nitrogen, oxygen, or sulfur.

More preferred $R^3$ groups of formula I are selected from C(O)NHR, C(O)R, C(R)=NOR, C(R)=NOH, or $CO_2R$, wherein:
each R is independently selected from a $C_{1-4}$ aliphatic group or T-Ar, wherein:
said $C_{1-4}$ aliphatic group is substituted with 0-2 groups independently selected from halogen, OR', or $N(R')_2$;
T is $(CH_2)_y$, wherein y is 0, 1, or 2; and
Ar is selected from pyrrolidinyl, furanyl, thiazolyl, tetrahydrofuranyl, pyrimidinyl, pyrazinyl, pyridyl, piperidinyl, imidazolyl, pyridazinyl, isoxazolyl, pyrazolyl, tetrahydropyranyl, or cyclopentene, wherein:
Ar is substituted with 0-2 groups independently selected from R', oxo, OR', or $N(R')_2$.

Most preferred $R^3$ groups of formula I are selected from $CO_2CH_3$, C(R)=NOR, C(R)=NOH, or C(O)NHR, wherein each R is independently selected from the following groups: cyclopropyl, $CH_2CH_2$(1-methylpyrrolidin-2-yl), $CH_2$(1-ethylpyrrolidin-2-yl), $CH_2CH_2$pyrrolidin-1-yl, $CH_2$furan-2-yl, thiazol-2-yl, $CH_2$tetrahydrofuran-2-yl, pyrimidin-2-yl, pyrazin-2-yl, $CH_2$pyridin-2-yl, pyridin-3-yl, pyridin-4-yl, $CH(CH_3)CH_2OCH_3$, $CH_2CF_3$, $CH_2CH_3$, $CH_2CH_2N(CH_2CH_3)_2$, $CH_2CH_2N(CH_3)_2$, $CH_2CH_2OCH_3$, $CH_2C\equiv CH$, $CH_2$cyclopropyl, 1-ethylpiperidin-3-yl, $CH(CH_2CH_3)CH_2OCH_3$, $CH(CH_3)CH_2OCH_3$, dihydro-furan-2-on-3-yl, 1-methyl-1,5-dihydro-imidazol-4-on-2-yl, pyridazin-4-yl, imidazol-2-yl, 3H-pyridin-4-on-2-yl, pyrimidin-5-yl, cyclpenten-4-yl, 1-methyl-imidazol-2-yl, tetrahydropyranyl, $CH_2$(3-methyl-isoxazol-5-yl), or $CH_2$(1,3-dimethyl-pyrazol-5-yl).

According to another embodiment, $R^3$ is preferably C(R)=NOR or C(R)=NOH.

According to another embodiment, $R^3$ is preferably C(O)R.

Preferably, $R^4$ of formula I is hydrogen or fluorine. More preferably, $R^4$ of formula I is hydrogen.

Compounds of the present invention fall within the genus of compounds described in PCT/US01/48855. However, applicants have discovered that the presence of the $R^3$ moiety, as defined above, imparts surprising and unexpectedly increased enzyme and antimicrobial potency.

According to a preferred embodiment, the present invention relates to a compound of formula II or IIa:

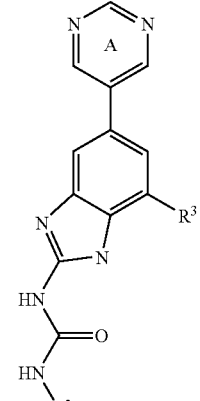

II

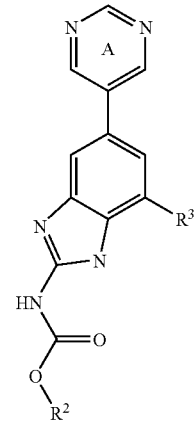

II' or a pharmaceutically acceptable salt thereof, wherein $R^2$ and $R^3$ are as defined above, and ring A is substituted with 0-2 groups independently selected from $N(R')_2$, OR', R, or SR'.

Preferred $R^2$ and $R^3$ groups of formulae II and II' are those described for formula I above.

According to another preferred embodiment, the present invention relates to a compound of formula III or III':

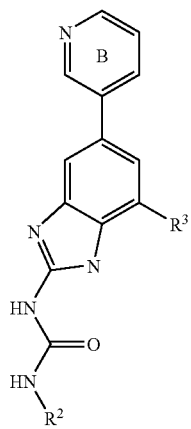

III

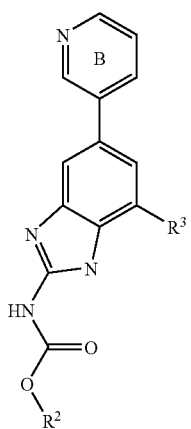

III' or a pharmaceutically acceptable salt thereof, wherein $R^2$ and $R^3$ are as defined above, and Ring B is optionally substituted with 0-2 groups independently selected from R or oxo, wherein R' is preferably hydrogen or $C_{1-3}$ aliphatic optionally substituted with) $N(R^O)_2$.

Preferred $R^2$ and $R^3$ groups of formulae III and III' are those described for formula I above.

According to another preferred embodiment, the present invention relates to a compound of formula III-a:

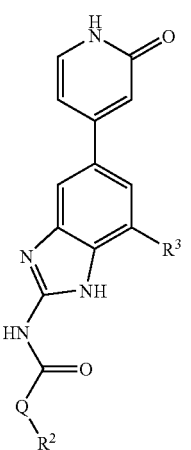

III-a or a pharmaceutically acceptable salt thereof, wherein $R^2$ and $R^3$ are as defined above, and the pyridone ring depicted is substituted with 0-2 groups independently selected from halogen, oxo, R, $CO_2R'$, OR', $N(R')_2$, SR', $C(O)N(R')_2$, NR'C(O)R', $SO_2R'$, $SO_2N(R')_2$, or $NR'SO_2R'$.

Preferred $R^2$ and $R^3$ groups of formula III-a are those described for formula I above.

Preferred substituents on the pyridone ring of formula III-a are those described above as preferred substituents on $R^1$ of formula I.

According to one embodiment, the present invention relates to a compound of formula III-a wherein Q is —NH—.

According to another embodiment, the present invention relates to a compound of formula III-a wherein Q is —O—.

According to another embodiment, the present invention relates to a compound of formula I wherein Q is —$CH_2$—.

According to another preferred embodiment, the present invention relates to a compound of formula III-b:

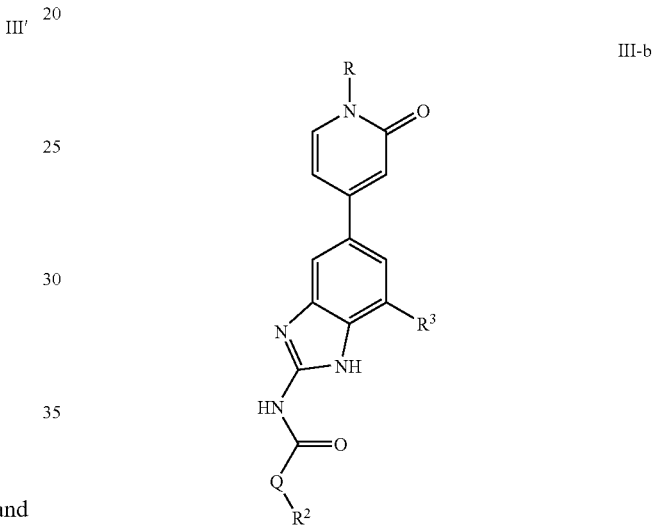

III-b or a pharmaceutically acceptable salt thereof, wherein R, $R^2$ and $R^3$ are as defined above Preferred $R^2$ groups of formula III-b are those described for $R^2$ groups of formula I above.

Preferred $R^3$ groups of formula III-b are those described for $R^3$ groups of formula I above.

Preferred R substituents on the pyridone ring of formula III-b are selected from T-Ar wherein Ar is an optionally substituted ring selected from a 5-6 membered heterocyclic ring having 1-3 heteroatoms independently selected from nitrogen, oxygen, or sulfur, or a 5-6 membered aryl ring having 0-3 heteroatoms independently selected from nitrogen, oxygen, or sulfur. Preferred Ar include phenyl or pyridyl. More preferred R substituents on the pyridone ring of formula III-b are selected from methyl, ethyl, t-butyl, isobutyl, cyclopropyl, isopropyl, $CH_2$phenyl, $CH_2$pyridin-3-yl, $CH_2$piperidinyl, $CH_2$cyclopropyl, or $CH_2CH_2OCH_3$.

According to one embodiment, the present invention relates to a compound of formula III-b wherein Q is —NH—.

According to another embodiment, the present invention relates to a compound of formula III-b wherein Q is —O—.

According to another embodiment, the present invention relates to a compound of formula I wherein Q is —$CH_2$—.

According to another preferred embodiment, the present invention relates to a compound of formula IV:

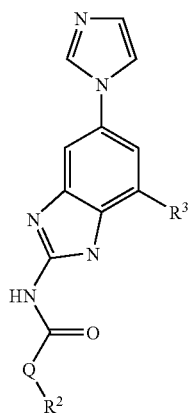

or a pharmaceutically acceptable salt thereof, wherein $R^2$ and $R^3$ are as defined above, and the imidazole ring depicted is optionally substituted in the 4-position with $C(O)N(R')_2$, oxo, and/or substituted in the 2-position with R.

Preferred $R^2$ and $R^3$ groups of formula IV are those described for formula I above.

According to one embodiment, the present invention relates to a compound of formula IV wherein Q is —NH—.

According to another embodiment, the present invention relates to a compound of formula IV wherein Q is —O—.

According to another embodiment, the present invention relates to a compound of formula I wherein Q is —CH$_2$—.

According to one embodiment, the present invention relates to a compound of formula I, II, III, III-a, III-b, or IV, or any subset thereof, wherein X is CH.

According to another embodiment, the present invention relates to a compound of formula I, II, III, III-a, III-b, or IV, or any subset thereof, wherein X is CF.

According to another embodiment, the present invention relates to a compound of formula I, II, III, III-a, III-b, or IV, or any subset thereof, wherein W is nitrogen.

According to another embodiment, the present invention relates to a compound of formula I, II, III, III-a, III-b, or IV, or any subset thereof, wherein W is C—$R^4$.

According to another embodiment, the present invention relates to a compound of formula I, II, III, III-a, III-b, or IV, or any subset thereof, wherein W is CH.

Exemplary structures of compounds of formula I are set forth in Table 1 below.

TABLE 1

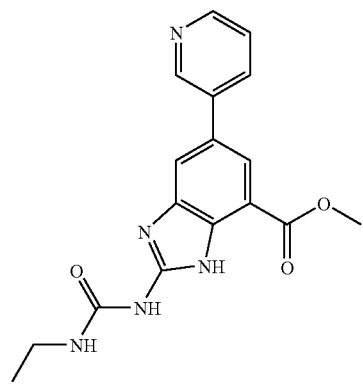

I-1

TABLE 1-continued

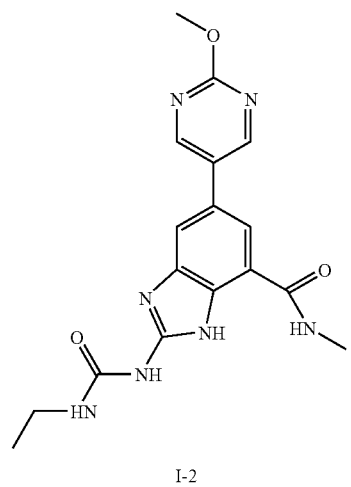

I-2

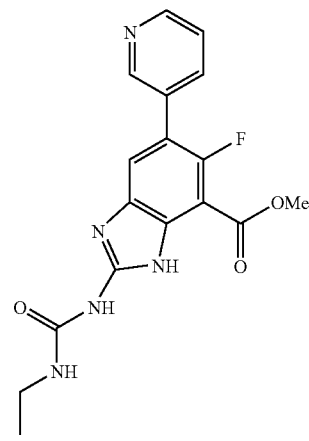

I-3

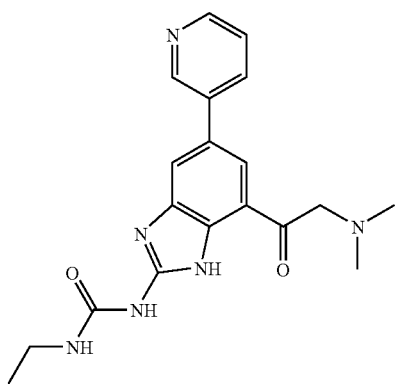

I-4

TABLE 1-continued
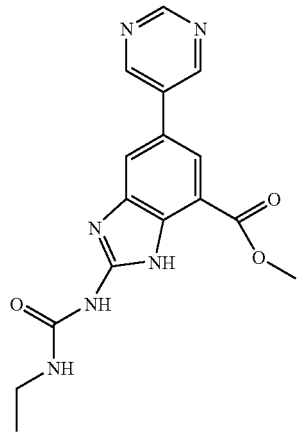
I-5
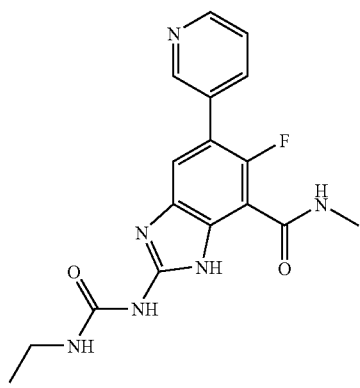
I-6
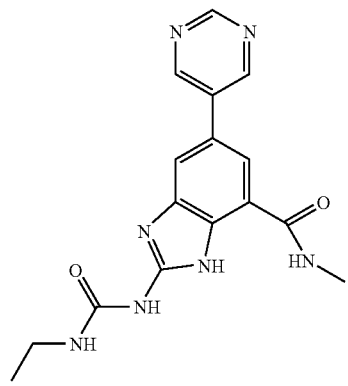
I-7
TABLE 1-continued
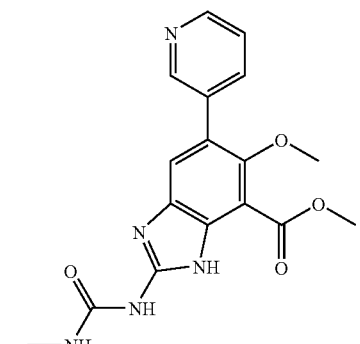
I-8
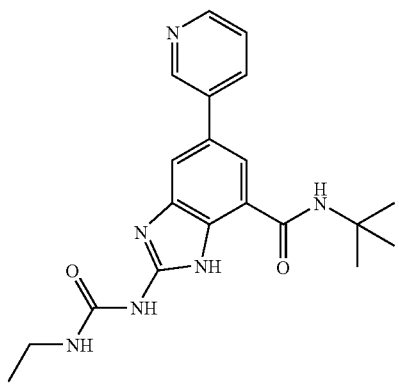
I-9
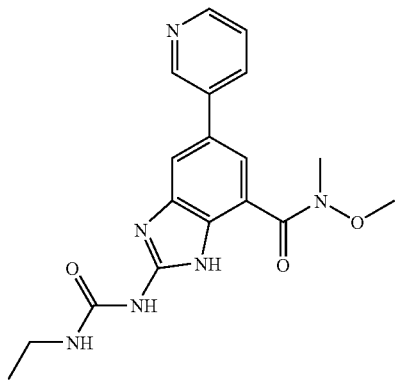
I-10

TABLE 1-continued
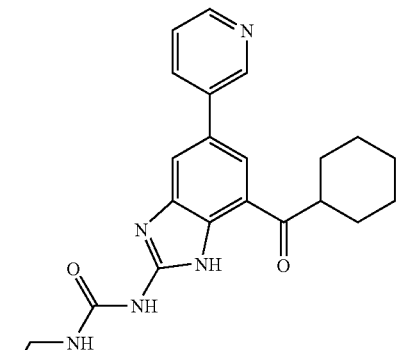
I-11
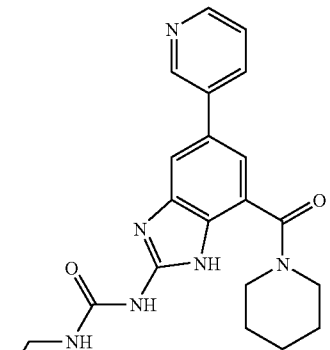
I-14
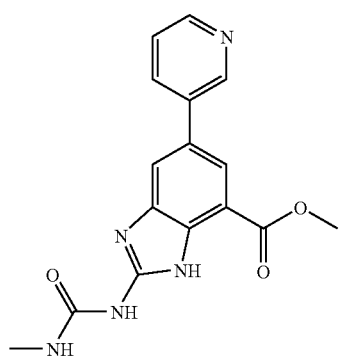
I-12
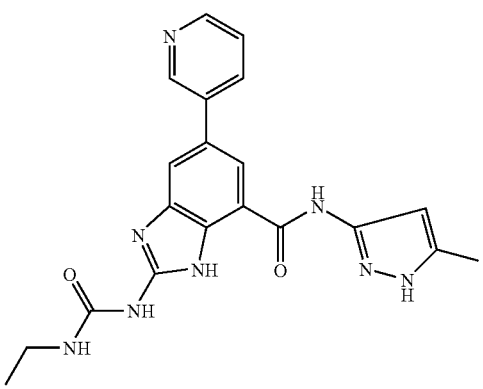
I-15
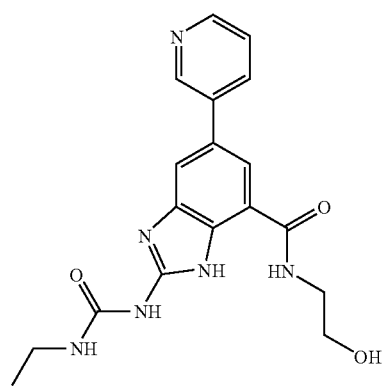
I-13
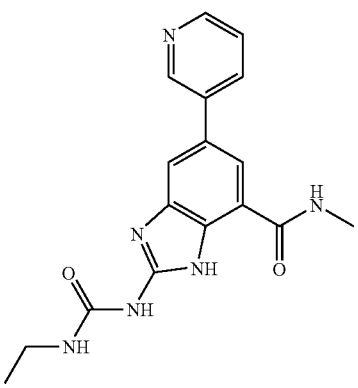
I-16

TABLE 1-continued
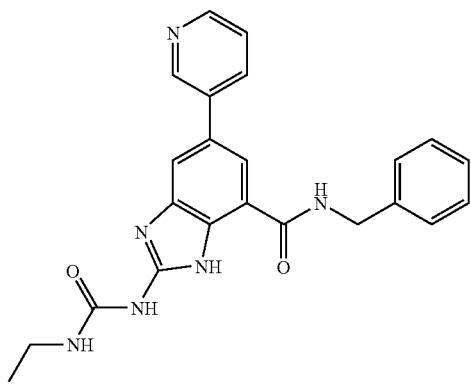
I-17
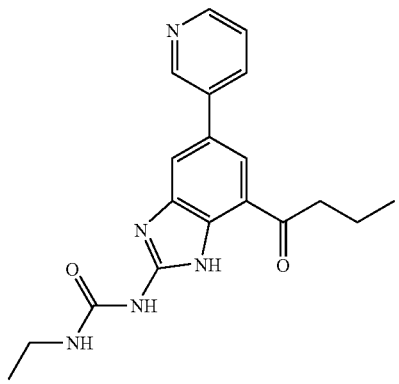
I-20
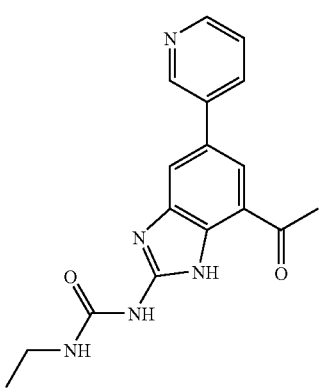
I-18
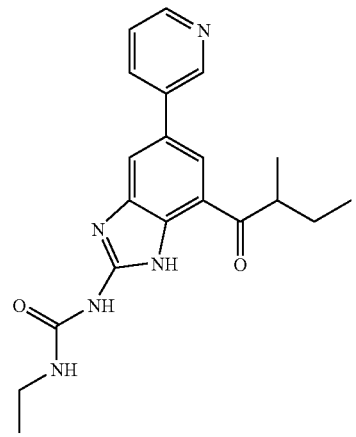
I-21
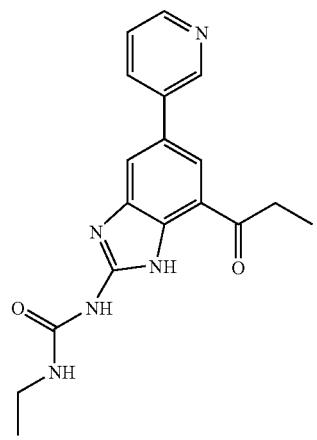
I-19
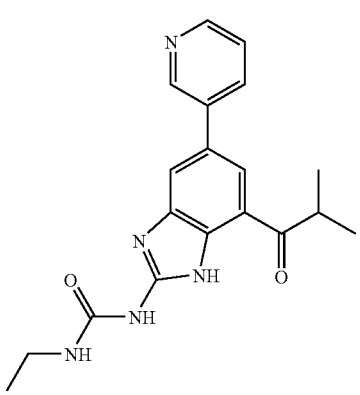
I-22

TABLE 1-continued
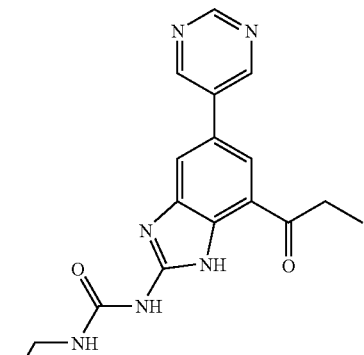
I-23
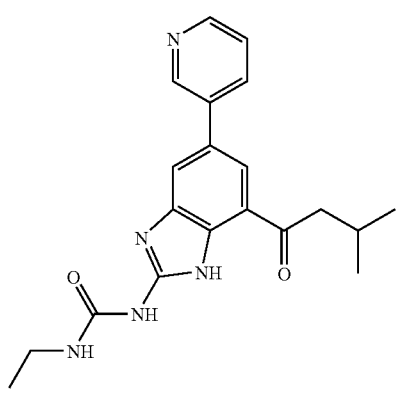
I-24
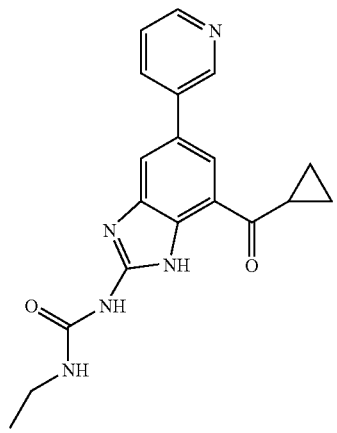
I-25
TABLE 1-continued
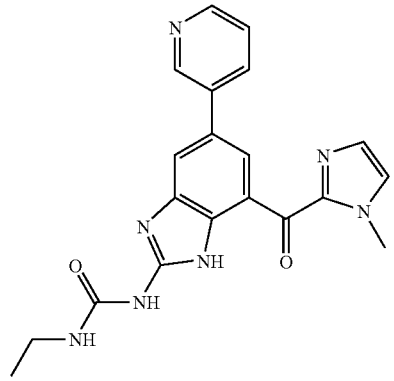
I-26
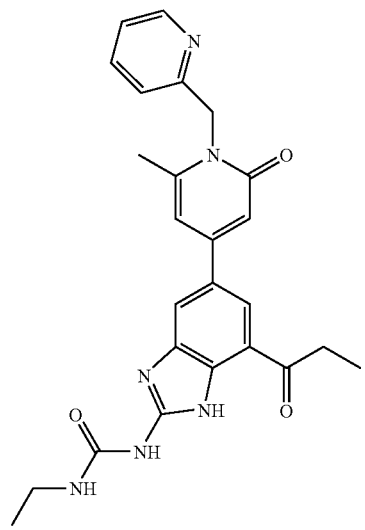
I-27
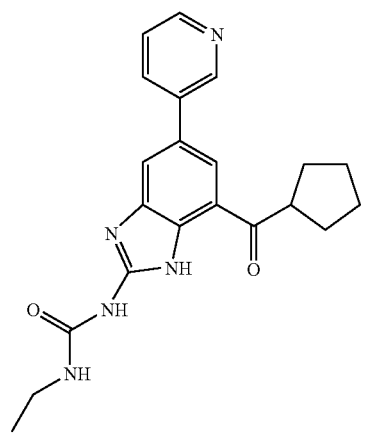
I-28

TABLE 1-continued
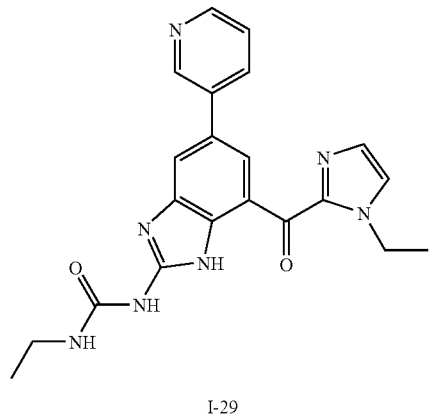
I-29
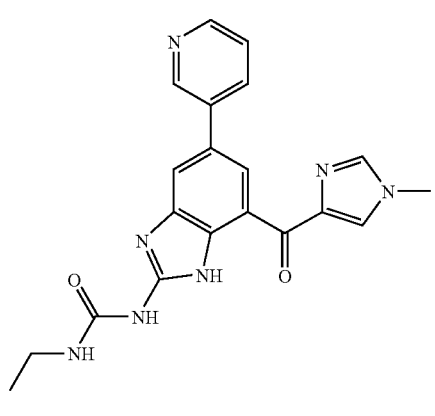
I-30
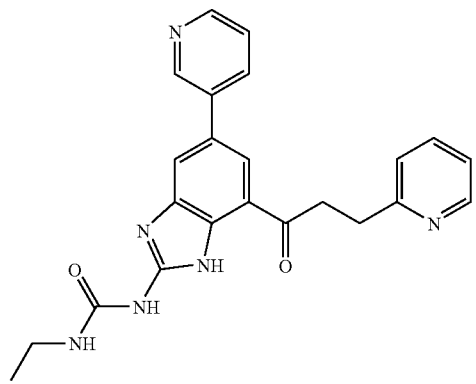
I-31
TABLE 1-continued
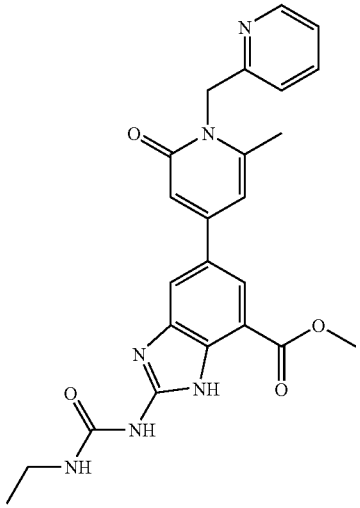
I-32
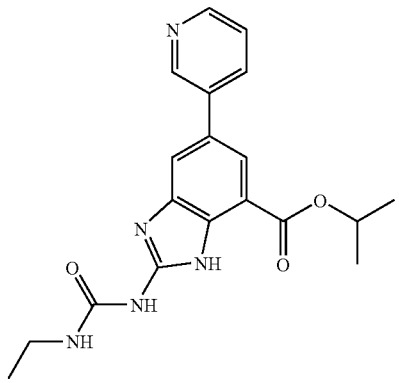
I-33
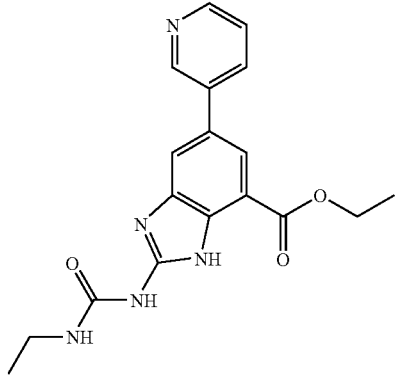
I-34

TABLE 1-continued
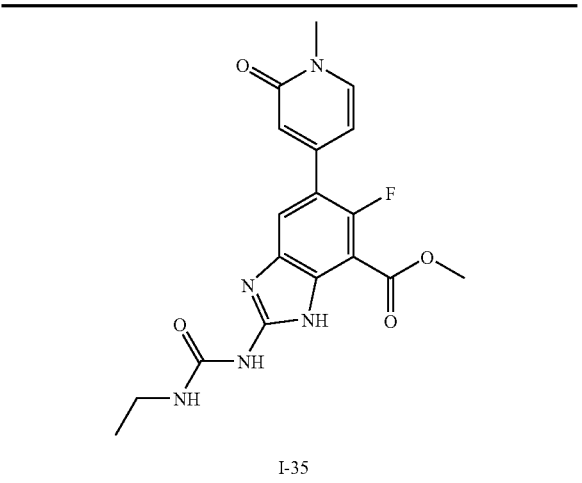
I-35
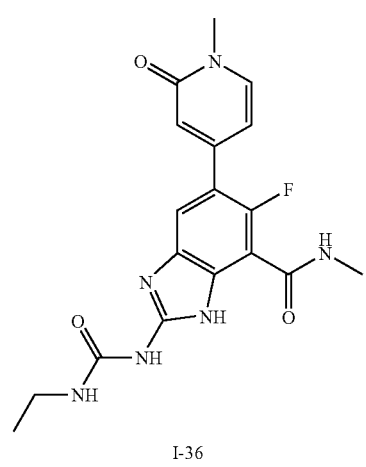
I-36
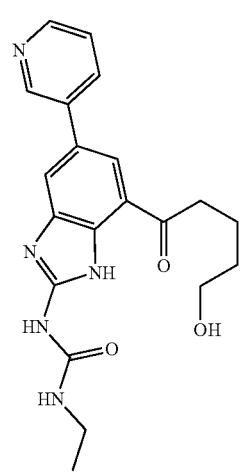
I-37
TABLE 1-continued
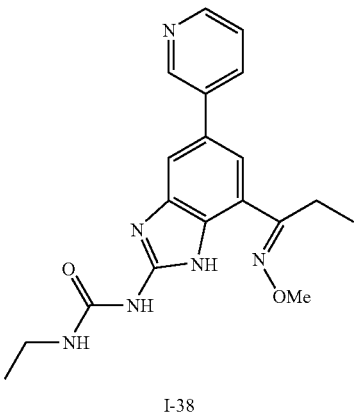
I-38
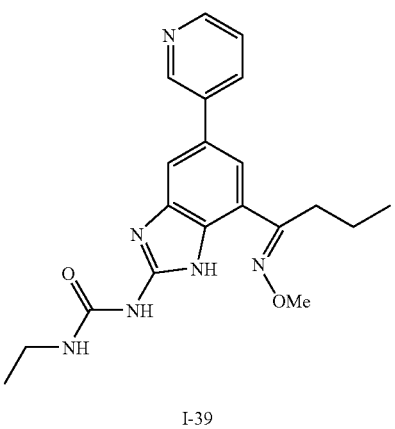
I-39
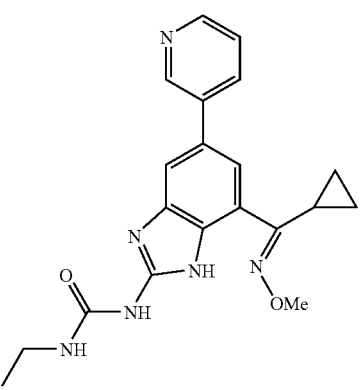
I-40

TABLE 1-continued

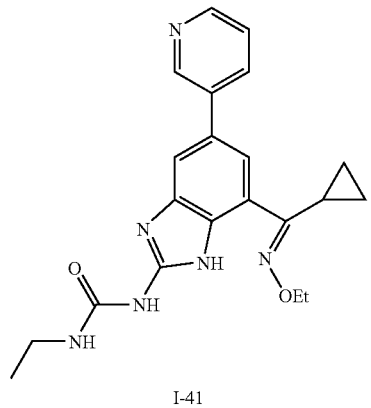

I-41

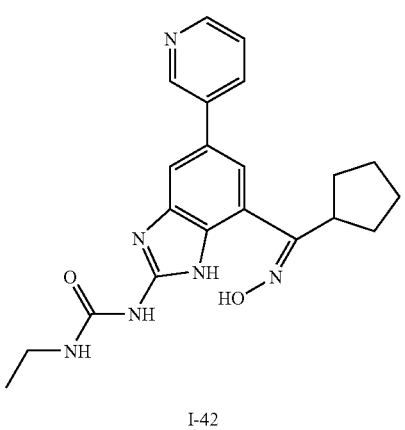

I-42

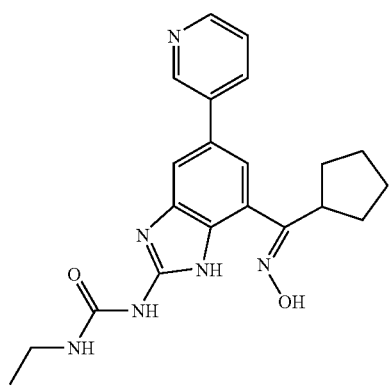

I-43

TABLE 1-continued

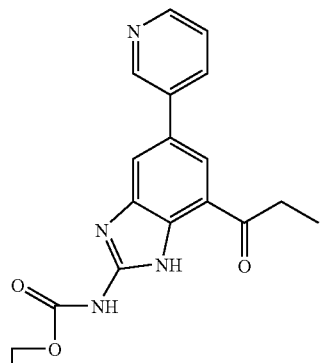

I-44

The compounds of this invention may be prepared by methods known to those skilled in the art for analogous compounds and as illustrated by the general Schemes I through IX shown below. The details of the conditions used for preparing these compounds are set forth in the Examples.

Scheme I

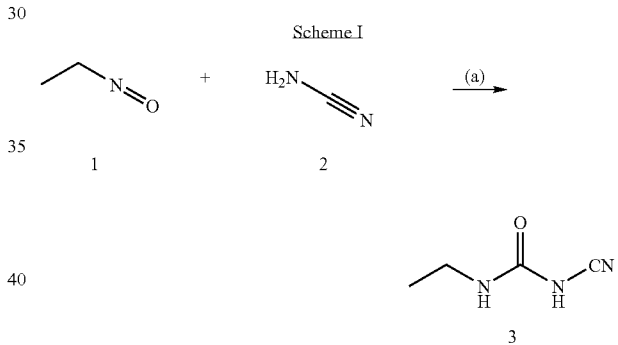

Scheme I above shows a general method for preparing N'-alkyl-N-cyanoureas (3) useful in the preparation of the compounds of the present invention. At step (a), cyanamide (2) is treated with ethyl isocyanate in the presence of base to afford, after acidification, compound 3. Although N'-ethyl-N-cyanourea is depicted, one of skill in the art would understand that a variety of alkyl isocyanates would be amenable to the reaction conditions of Scheme I to form a variety of N'-alkyl-N-cyanoureas.

At step (a), cyanamide (2) may be treated with alkyl isocyanate in the presence of a variety of bases to form the cyanourea (3). Suitable bases useful for the formation of 3 include hydride bases, such as NaH and KH, metal alkoxides, such as sodium t-butoxide and potassium t-butoxide, and metal hydroxides, such as sodium hydroxide, potassium hydroxide, cesium hydroxide, and lithium hydroxide.

At step (a), metal-hydride, metal-alkoxide, and metal-hydroxide bases are used to form a metal salt of the cyanourea (3), having the formula 3a:

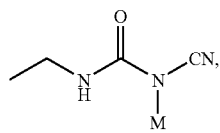

wherein M is sodium, Li, K, Rb, or Cs. Preferably, M is sodium.

Step (a) is performed in a variety of solvents including THF, alcohols, methylene chloride, DME, EtOAc, iPrOAc, chlorobenzene, methyl t-butyl ether, toluene, heptane, and cyclohexane. Preferably, the solvent used for step (a) is an anhydrous solvent. More preferably, the solvent used for step (a) is anhydrous THF.

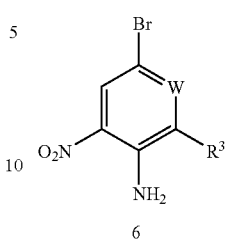

Scheme III

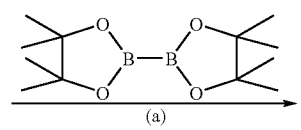

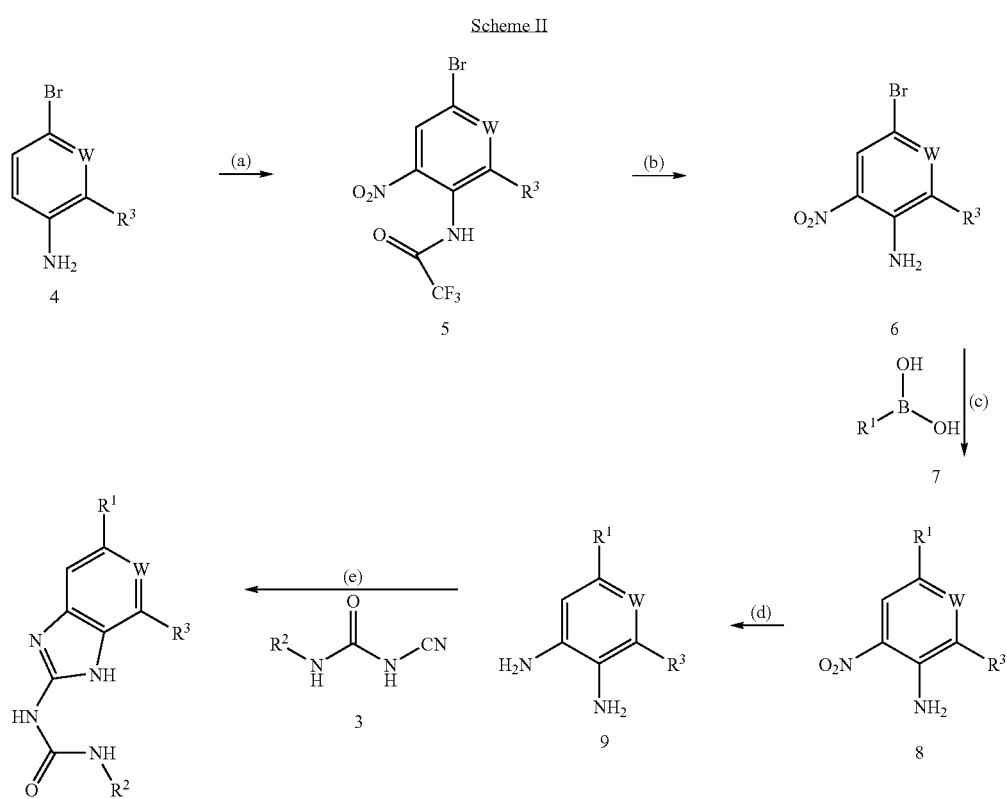

Reagents and conditions:(a) *i* trifluoroacetic anhydride, *ii* potassium nitrate; (b) HCl, MEOH; (c) NaHCO3, tetrakistriphenylphosphine-Pd(0); (d) H₂, Pd/C; (e) H₂SO₄.

Scheme II above shows a general method for preparing the benzimidazole compounds of the present invention. The bromo-aniline (4) is treated with trifluoroacetic anhydride then potassium nitrate to form the nitro compound (5) which is then deprotected by treatment with acid to form the amine (6). The 3-nitro-5-bromoaniline (6) is then coupled to an aryl boronic acid (7) in the presence of palladium to form the bi-aryl compound (8). The nitro group of compound 8 is reduced to form the diamine compound 9 which is treated with an N'-alkyl-N-cyanourea to form the benzimidazole compounds of this invention (10). The reactions depicted in Scheme II above are amenable to a variety of $R^1$ and $R^3$ groups of the present invention.

-continued

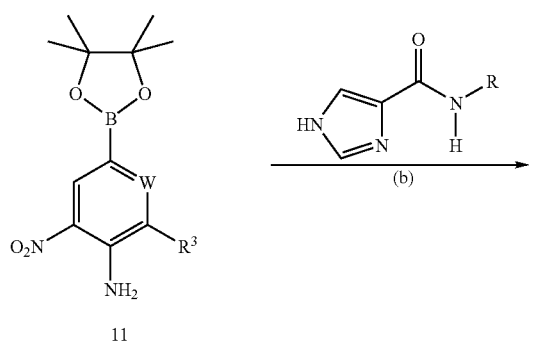

-continued

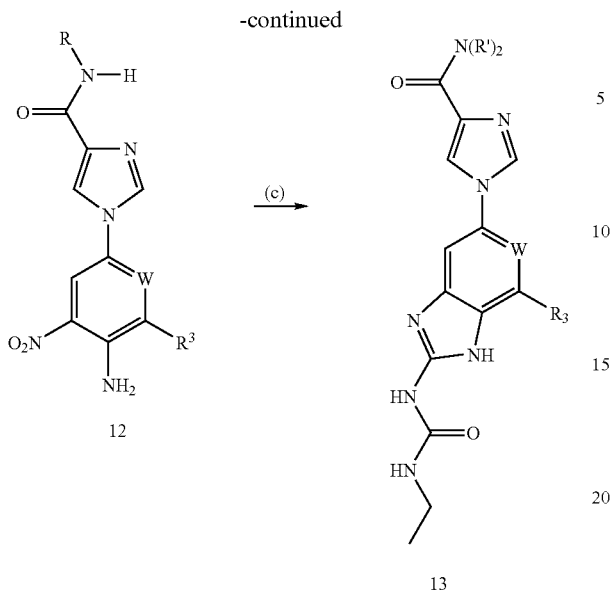

Reagents and conditions: (a) Pd (dppf)Cl2/KOAc, DMSO, 80°C; (b) Cu(OAc) Cu(OAc)₂/pyridine, DMF; (c) i H₂, Pd/C, ii 3, H₂SO₄-

Scheme III above shows a general method for preparing compounds of formula IV substituted in the 4-position with $C(O)N(R')_2$ using methods substantially similar to those described by Kiyomori, A. and Marcoux, J.-F.; Buchwald, S. L., *Tetrahedron Letters*, vol. 40, 1999, 2657-2660. Compound 6 is treated with diboranic ester in the presence of Pd(dppf)/potassium acetate in DMSO at 80° C. to afford intermediate 11. Compound 11 is treated with 4-C(O)N(R')₂-imidazole in the presence of copper acetate to form the 4-C(O)N(R')₂-imidazol-1-yl compound 12. The nitro group of compound 12 is reduced to form the diamine which is in turn treated with N'-ethyl-N-cyanourea (3) to form the benzimidazole compound 13 as described in Scheme II, step (e).

Scheme IV

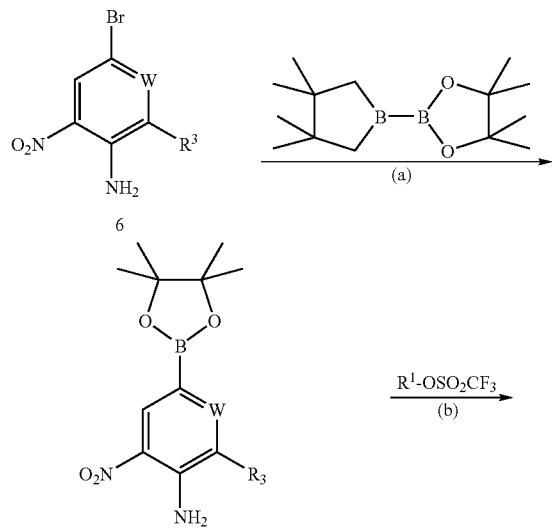

-continued

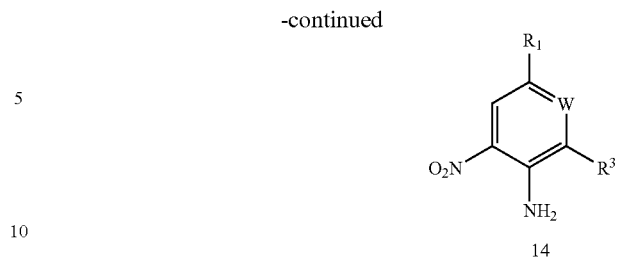

Scheme IV above shows an alternate general method for preparing compounds of formula I. Compound 6 is treated with bispinacoladiboron in the presence of Pd(dppf)/potassium acetate to afford intermediate 11, as described above for Scheme III. Compound 11 is then treated with $R^1$-triflate in the presence of tetrakistriphenylphosphinepalladium, lithium chloride, and sodium carbonate to form compound 14. Compound 14 can then be used to prepare compounds of the present invention by methods substantially similar to those recited above at Schemes I through III.

Scheme V

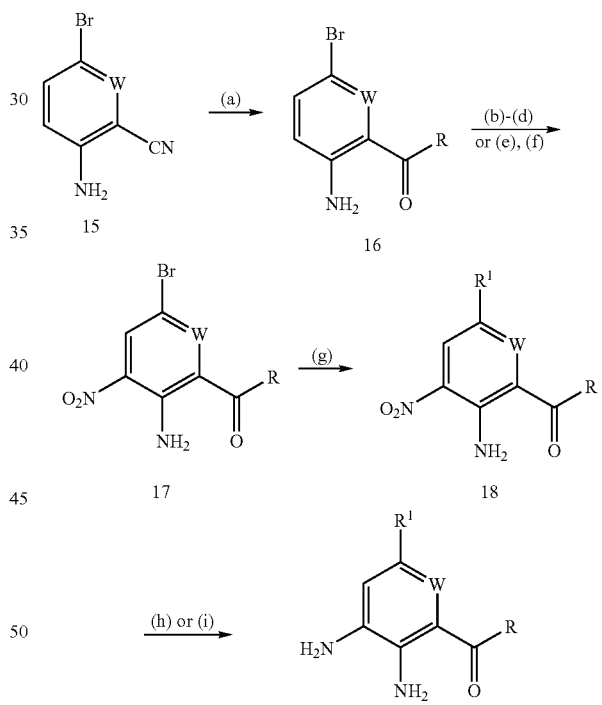

Reagents and conditions: (a) R-magnesium halide, THF, 0°C to rt; (b) Ac₂O, 80°C (c); HNO₃; (d) 6N aq. HCl; (e) trifluoroacetic acid anhydride then KNO₃; (f) Na₂CO₃, MeOH/H₂O (9:1), 65°C; (g)R¹-boronate, Pd(PPh₃)₄, 1N aq. NaHCO₃, DME, 90°C; (h) SnCl₂.2H₂O, EtOH, reflux; and (i) Na₂S₂O₄, EtOH/H₂O (3:1), 90°C.

Scheme V above shows general method for preparing compounds of formula I wherein $R^3$ is C(O)R. The cyano compound 15 is treated with R-magnesium halide to form the ketone 16. The nitro compound 17 is prepared from 16 by treating with acetic anhydride then nitric acid. Alternatively, 17 can be prepared by treating 16 with trifluoroacetic anydride and potassium nitrate. The nitro compound 17 is then treated with the boronate, as described above, to form compound 18. The nitro group of compound 18 is reduced to form the diamine compound 19 either with SnCl$_2$ (step h) or Na$_2$S$_2$O$_4$ (step i). The diamine compound 19 can then be used to prepare compounds of formula I, wherein R$^3$ is C(O)R, by methods substantially similar to those set forth at Schemes I through IV above.

Scheme VI

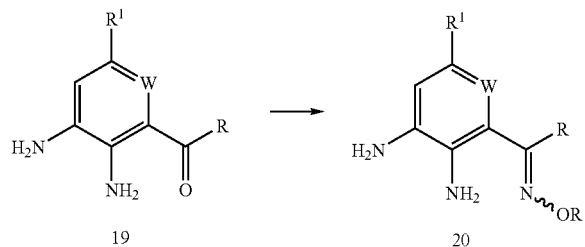

Scheme VI above shows general method for preparing compounds of formula I wherein R$^3$ is C(R)=NOR. The ketone compound 19 is treated with potassium acetate and HCl.NH—OR to form the oxime compound 20. Compound 20 can then be used to prepare compounds of formula I wherein R$^3$ is C(R)=NOR using methods substantially similar to those set forth for Schemes I-IV above.

Scheme VII

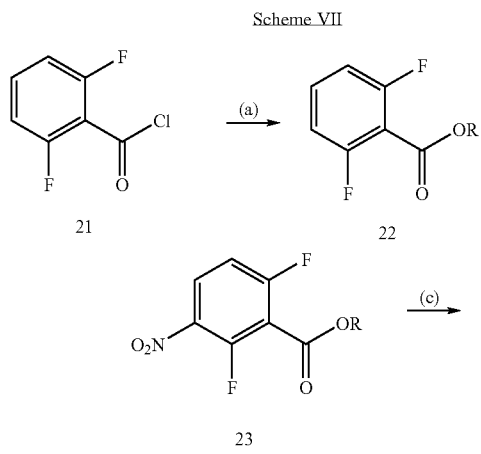

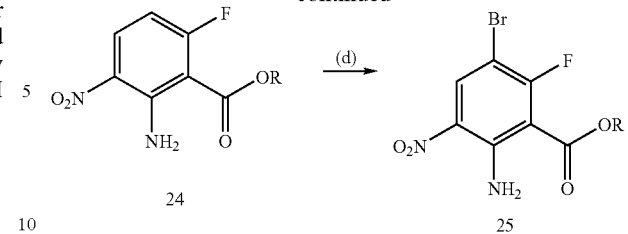

Scheme VII above shows general method for preparing compounds of formula I wherein W is CF and R$^3$ is CO$_2$R. Compound 24 is prepared from commercially available starting materials by methods substantially similar to those described by Kim, K. S., et al, *J. Med. Chem.* 1993, 36, 2335. Compound 25 is prepared by treating compound 24 with bromine in acetic acid. Compounds of the present invention wherein R$^3$ is CO$_2$R can be prepared from compound 25 by methods substantially similar to those described above at Schemes I through IV.

Scheme VIII

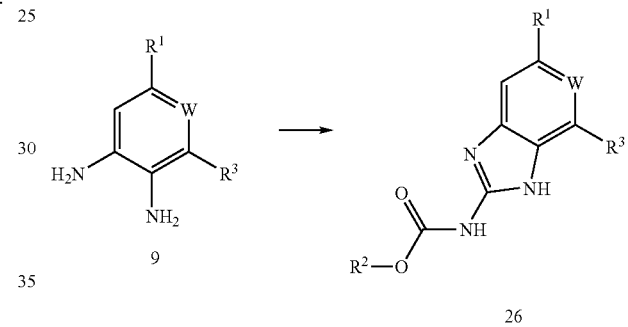

Scheme VIII above shows a general method for preparing compounds of the present invention wherein Q is —O—. Compound 9, prepared according to Scheme II above, is treated with 2-methyl-2-thiopseudourea and R$^2$-chloroformate to form compound 26. This method is generally described by L. I. Kruse et al, *J. Med. Chem.* 1989, 32, 409-417.

Scheme IX

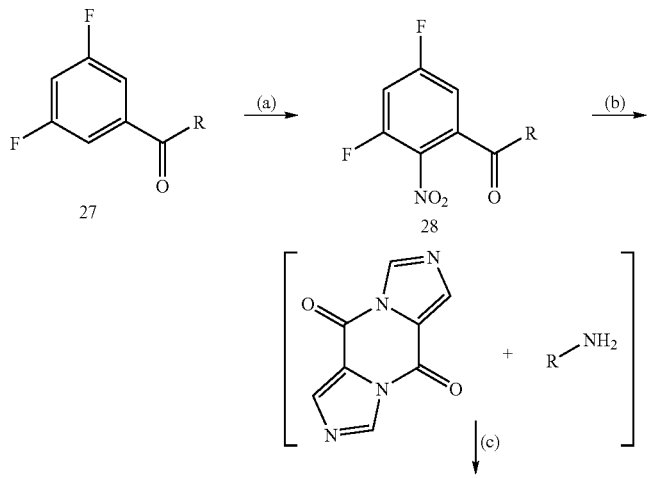

-continued

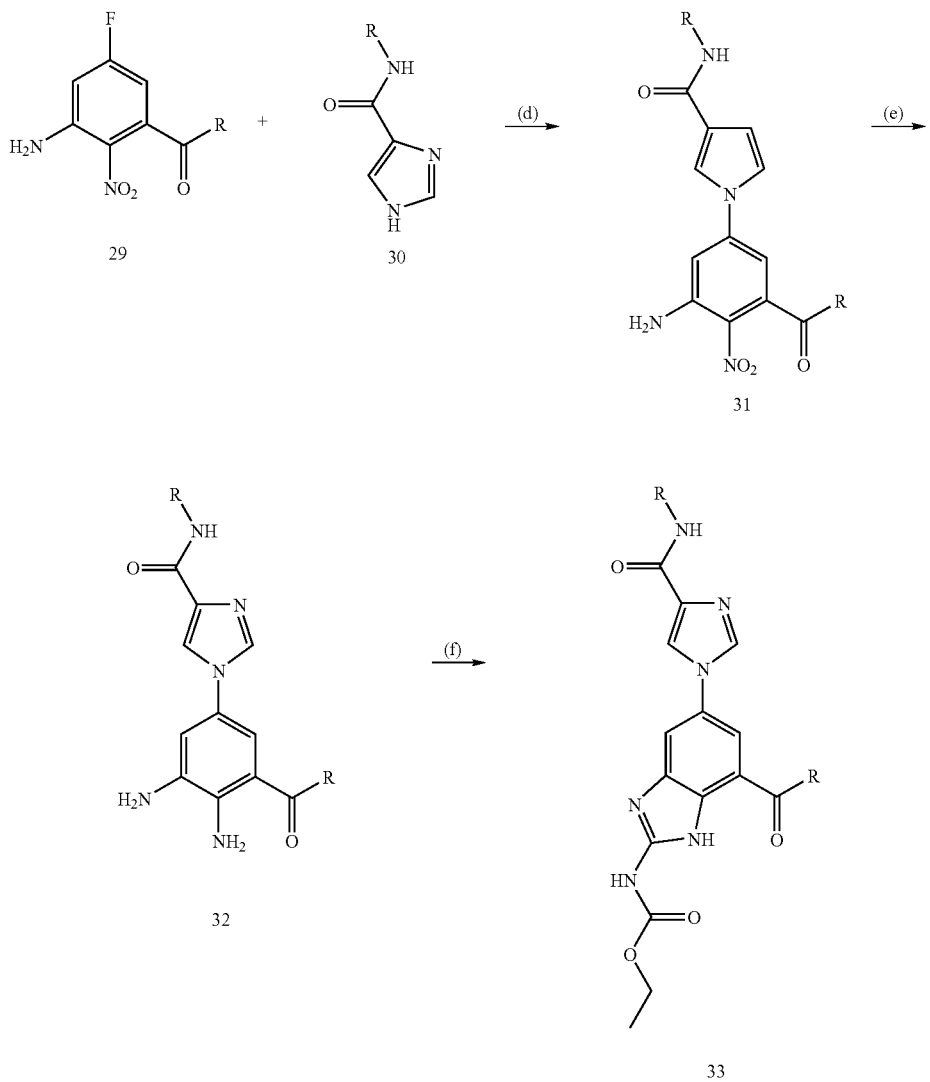

Reagents and conditions: (a) $HNO_3/H_2SO_4$; (b) $NH_4OH$/dioxane/heat; (c) dioxane/heat; (d) $Na_2CO_3$/DMF/heat; (e) $H_2$/Pd-C/EtOH; (f) by methods above Scheme IX above depicts an alternate general method for preparing compounds of the present invention wherein $R^1$ is imidazol-1-yl. At step (a), the difluoro ketone is treated with nitric acid to form the nitro compound 28. Compound 28 is then treated with ammonium hydroxide to form the amino-nitro compound 29. The mono-fluoro compound 29 can then be coupled to the imidazole 30 to form compound 31. Compound 31 is then used to prepare various compounds of the present invention using the methods described above for preparing compounds wherein Q is —$CH_2$—, —NH— or —O—.

One of skill in the art would recognize that a variety of compounds of the present invention may be prepared according to the general method of Schemes I through IX, and the synthetic Examples set forth below.

According to another embodiment, the present invention relates to a method for preparing a compound of formula A:

A

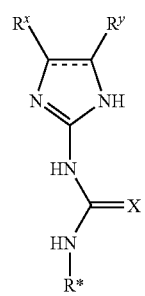

or a salt thereof, comprising the step of reacting a compound of formula B:

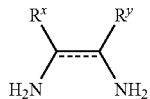

or a salt thereof, with a compound of formula C:

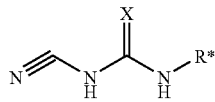

or a salt thereof, wherein said reaction is performed in a non-basic medium containing at least one protic solvent, wherein:

X is oxygen or sulfur;

$R^x$ and $R^y$ are independently selected from $R^5$, $OR^5$, $N(R^5)_2$, $C(O)N(R^5)_2$, $CO_2R^5$, or $R^x$ and $R^y$ are taken together to form a 5-8 membered saturated, partially unsaturated, or aryl ring having 0-3 heteroatoms independently selected from nitrogen, oxygen, or sulfur, and wherein:

said ring formed by $R^x$ and $R^y$ is optionally substituted with 1-3 groups independently selected from oxo, halogen, $R^1$, $R^3$, $R^5$, $OR^5$, $N(R^5)_2$, $OC(O)R^5$, $NR^5C(O)R^5$, or $R^6$;

$R^1$ is a 5-6 membered aryl ring having 1-3 heteroatoms independently selected from oxygen, nitrogen, or sulfur, wherein:

$R^1$ is substituted with 0-3 groups independently selected from R, oxo, $CO_2R'$, $OR'$, $N(R')_2$, $SR'$, $NO_2$, halogen, CN, $C(O)N(R')_2$, $NR'C(O)R'$, $SO_2R'$, $SO_2N(R')_2$, or $NR'SO_2R'$;

each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:

R' is substituted with 0-3 groups independently selected from halogen, oxo, $R^o$, $N(R^o)_2$, $OR^o$, $CO_2R^o$, $NR^oC(O)R^o$, $C(O)N(R^o)_2$, $SO_2R^o$, $SO_2N(R^o)_2$, or $NR^oSO_2R^o$;

$R^3$ is selected from C(O)NHR, $C(O)N(R)_2$, COR, $CO_2R$, COCOR, $SO_2R$, $SO_2N(R)_2$, $SO_2NHR$, C(R)=NOH, C(R)=NOR, C(R)=NR, or C(R)=N—NHR;

each R is independently selected from T-Ar or a $C_{1-6}$ aliphatic group, wherein:

said $C_{1-6}$ aliphatic group is substituted with 0-3 groups independently selected from R', oxo, $CO_2R'$, $OR'$, $N(R')_2$, $SR'$, $NO_2$, halogen, CN, $C(O)N(R')_2$, $NR'C(O)R'$, $SO_2R'$, $SO_2N(R')_2$, or $NR'SO_2R'$;

T is $(CH_2)_y$, wherein y is 0, 1, or 2;

Ar is selected from:
(a) a 3-8 membered saturated, unsaturated, or aryl ring;
(b) a 3-7 membered heterocyclic ring having 1-3 heteroatoms independently selected from nitrogen, oxygen, or sulfur; or
(c) a 5-6 membered heteroaryl ring having 1-3 heteroatoms independently selected from nitrogen, oxygen, or sulfur, wherein:

Ar is substituted with 0-3 groups independently selected from R', oxo, $CO_2R'$, $OR'$, $N(R')_2$, $SR'$, $NO_2$, halogen, CN, $C(O)N(R')_2$, $NR'C(O)R'$, $SO_2R'$, $SO_2N(R')_2$, or $NR'SO_2R'$;

each $R^5$ is independently selected from hydrogen, a $C_{1-6}$ aliphatic group, or a 5-6 membered saturated, partially unsaturated, or aryl ring having 0-3 heteroatoms independently selected from nitrogen, oxygen, or sulfur, wherein:

$R^5$ is optionally substituted with 1-3 groups independently selected from halogen, halogen, oxo, $R^o$, $N(R^o)_2$, $OR^o$, $CO_2R^o$, $NR^oC(O)R^o$, $C(O)N(R^o)_2$, $SO_2R^o$, $SO_2N(R^o)_2$, or $NR^oSO_2R^o$;

each $R^o$ is independently selected from hydrogen, $C_{1-6}$ aliphatic, phenyl, or a 5-6 membered heteroaryl or heterocyclyl ring having 1-2 heteroatoms independently selected from nitrogen, oxygen, or sulfur; and R* is selected from $R^2$, $C_{1-6}$ aliphatic, or a 5-6 membered saturated, partially unsaturated, or aryl ring having 0-3 heteroatoms independently selected from nitrogen, oxygen, or sulfur, wherein:

$R^2$ is selected from hydrogen or $C_{1-3}$ aliphatic group; and

R* is optionally substituted with 1-3 groups independently selected from halogen, halogen, oxo, $R^o$, $N(R^o)_2$, $OR^o$, $CO_2R^o$, $NR^oC(O)R^o$, $C(O)N(R^o)_2$, $SO_2R^o$, $SO_2N(R^o)_2$, or $NR^oSO_2R^o$.

According to a preferred embodiment, $R^x$ and $R^y$ are taken together to form a 6-7 membered saturated, partially unsaturated, or aryl ring having 0-2 heteroatoms independently selected from nitrogen, oxygen, or sulfur and wherein said ring is optionally substituted. More preferably, $R^x$ and $R^y$ are taken together to form an optionally substituted 6 membered aryl ring having 0-2 heteroatoms independently selected from nitrogen, oxygen, or sulfur. Most preferably $R^x$ and $R^y$ are taken together to form a benzo ring substituted with one $R^1$ group and one $R^3$ group.

When $R^x$ and $R^y$ are taken together to form an optionally substituted 6-7 membered saturated ring having 0-2 heteroatoms independently selected from nitrogen, oxygen, or sulfur, the two amino groups as depicted in formula B are preferably in the cis configuration.

According to another preferred embodiment, R* is $R^2$. More preferably, R* is ethyl.

As used herein, the term "non-basic medium" means any solvent or mixture of at least two of solvent, co-solvent, and acid that results in a pH of less than or equal to about 7. Solvents that are suitable for the method include, but are not limited to, water, benzene, toluene, dichloromethane, dichloroethane, dimethylformamide, dioxane, dimethylsulfoxide, diglyme, momoglyme, acetonitrile, tetrahydrofuran, methanol, and ethanol.

As used herein, the term "protic solvent" means a proton-bearing solvent as described in "Advanced Organic Chemistry", Jerry March, 3$^{rd}$ edition, John Wiley and Sons, N.Y. Preferably the protic solvent is selected from water, ethanol, or methanol. In an alternative embodiment, an organic acid, such as acetic acid, may serve as both the protic solvent and acid components of the reaction.

According to another preferred embodiment, the method is performed at a pH of about 2 to about 7. More preferably, the pH is about 3 to about 4.

Suitable acids that may be added to the reaction mixture to achieve the non-basic medium include mineral acids. Examples of organic acids that may be used include, but are not limited to, mineral acids such as sulfuric, hydrochloric, and nitric. Preferably the acid is sulfuric or hydrochloric. More preferably the acid is sulfuric.

The method can be carried out at 20-155° C. Preferably, the method is heated at 40-100° C., and more preferably at 80-100° C.

According to another preferred embodiment, the present invention relates to a method for preparing a compound of formula I':

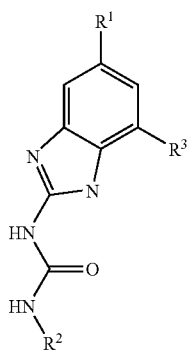

I' or a pharmaceutically acceptable salt thereof, comprising the step of reacting a compound of formula B':

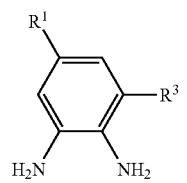

B' or a salt thereof, with a compound of formula C':

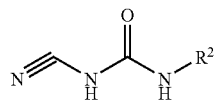

C' or a salt thereof, in a non-basic medium containing at least one protic solvent, wherein $R^1$, $R^2$, and $R^3$ are as defined above.

According to another embodiment, the present invention relates to a compound of formula C":

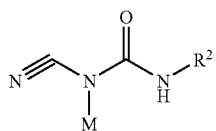

C"

wherein:

$R^2$ is selected from hydrogen, ethyl, isopropyl, cyclopropyl, or propyl; and

M is selected from sodium, potassium, lithium, cesium, or rubidium.

Preferably M is sodium or potassium. More preferably M is sodium.

Preferably $R^2$ is ethyl.

The compounds of this invention are potent inhibitors of gyrase and/or Topo IV as determined by enzymatic assay. These compounds have also been shown to have antimicrobial activity in an antimicrobial susceptibility assay. The activity of a compound utilized in this invention as an inhibitor of gyrase and/or Topo IV may be assayed in vitro, in vivo or in a cell line according to methods known in the art. The details of the conditions used for both the enzymatic and the antimicrobial susceptibility assays are set forth in the Examples below.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit gyrase, Topo IV, or to measurably decrease bacterial quantity, in a biological sample or in a patient. Preferably the composition of this invention is formulated for administration to a patient in need of such composition. Most preferably, the composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of gyrase and/or Topo IV activity in a biological sample is useful for a variety of purposes that are known to one of skill in the art. Examples of such purposes include, but are not limited to, blood transfusion, organ-transplantation, biological specimen storage, and biological assays.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in gyrase and/or Topo IV, activity between a sample comprising said composition and gyrase and/or Topo IV, and an equivalent sample comprising gyrase and/or Topo IV in the absence of said composition.

As used herein, the term "measurably decrease bacterial quantity", as used herein means a measurable change in the number of bacteria between a sample containing said composition and a sample containing only bacteria.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of gyrase and/or Topo IV.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium,*

*Klebsiella pneumoniae, Enterobacter* sps. *Proteus* sps. *Pseudomonas aeruginosa, E. coli, Serratia marcesens, Staphylococcus aureus,* Coag. Neg. Staph, *Haemophilus infuenzae, Bacillus anthracis, Mycoplasma pneumoniae, Moraxella catarralis, Chlamydia pneumoniae, Legionella pneumophila, Mycobacterium tuberculosis, Helicobacter pylori, Staphylococcus epidermidis,* or *Mycobacterium tuberculosis.*

Typically, the pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated". Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, or an agent which increases the susceptibility of bacterial organisms to antibiotics.

Examples of antibiotics suitable for administration with the compounds of the present invention, and compositions thereof, include quinolones, β-lactams, macrolides, glycopeptides, and lipopeptides.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395-411, and the sensitization of gram-negative bacteria has been described by Tsubery, H., et al, in *J. Med. Chem.* (2000) pp. 3085-3092.

According to another embodiment, the invention provides a method for treating or lessening the severity of a bacterial infection in a patient comprising the step of administering to said patient a composition according to the present invention.

According to another embodiment, the invention provides a method of inhibiting gyrase in a patient comprising the step of administering to said patient a composition according to the present invention.

According to another embodiment, the invention provides a method of inhibiting Topo IV in a patient comprising the step of administering to said patient a composition according to the present invention.

According to another embodiment, the invention provides a method of decreasing bacterial quantity in a patient comprising the step of administering to said patient a composition according to the present invention.

According to another embodiment, the invention provides a method of inhibiting gyrase in a biological sample.

According to another embodiment, the invention provides a method of inhibiting Topo IV in a biological sample.

According to another embodiment, the invention provides a method of decreasing bacterial quantity in a biological sample.

According to another embodiment, the invention provides a method of decreasing bacterial quantity in a biological sample, but further comprising the step of contacting said biological sample with an agent which increases the susceptibility of bacterial organisms to antibiotics.

The pharmaceutical compositions and methods of this invention will be useful generally for controlling bacterial infections in vivo. Examples of bacterial organisms that may be controlled by the compositions and methods of this invention include, but are not limited to, the following organisms: *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus,* Coag. Neg. Staph, *Haemophilus infuenzae, Bacillus anthracis, Mycoplasma pneumoniae, Moraxella catarralis, Chlamydia pneumoniae, Legionella pneumophila, Mycobacterium tuberculosis, Helicobacter pylori, Staphylococcus epidermidis,* or *Mycobacterium tuberculosis.*

According to another embodiment, bacterial organisms that may be controlled by the compositions and methods of this invention include the following organisms: *Streptococcus pneumoniae, Streptococcus pyogenes, Enterococcus faecalis, Enterococcus faecium, Staphylococcus aureus,* Coag. Neg. *Staph, Haemophilus infuenzae, Bacillus anthracis, Mycoplasma pneumoniae, Moraxella catarralis, Chlamydia pneumoniae, Legionella pneumophila, Mycobacterium tuberculosis, Helicobacter pylori, Staphylococcus epidermidis,* or *Mycobacterium tuberculosis.*

The compositions and methods will therefore be useful for controlling, treating or reducing the advancement, severity or effects of nosocomial or non-nosocomial infections. Examples of nosocomial uses include, but are not limited to, urinary tract infections, respiratory infections such as pneumonia, surgical wound infections, central line infection, and bacteremia. Examples of non-nosocomial uses include but are not limited to urinary tract infections, bronchitis, sinusitis, pneumonia, prostatitis, skin and soft tissue infections, intra-abdominal infections, and therapy for febrile neutropenic patients.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

In order that this invention be more fully understood, the following examples are set forth. These examples are for the purpose of illustration only and are not to be construed as limiting the scope of the invention in any way.

EXAMPLES

As used herein, the term "$R_t$," refers to the retention time, in minutes, obtained for the specified compound using the following HPCL method (unless stated otherwise):

Column: Zorbax SB Phenyl, 5 μm, 4.6 mm×250 mm
Gradient: water:acetonitrile (9:1) to (1:9) over 10 minutes.
Flow rate: 1.0 mL/minute
Wavelength: 214 nm.

Example 1

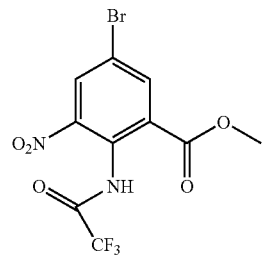

Methyl 5-bromo-3-nitro-2N-trifluoroacetylamino benzoate: Methyl-2-amino-5-bromo benzoate (5.0 g, 21.73 mmol) was added over a 5 minute period to trifluoroacetic anhydride (60 mL), cooled to 0-5° C. After stirring for an additional 15 minutes, potassium nitrate (2.637 g, 26.08 mmol) was added and the resulting beige slurry was stirred overnight. The reaction mixture was concentrated under reduced pressure to afford a tan solid, which was partitioned in sodium bicarbonate (aqueous, saturated) and extracted into ethyl acetate (3×). The combined organic layers were washed with brine, dried over sodium sulfate, filtered and concentrated under reduced pressure to provide 6.39 g of the title compound as a tan solid. HPLC $R_t$=3.62 minutes. MS (M−1 370.9).

Example 2

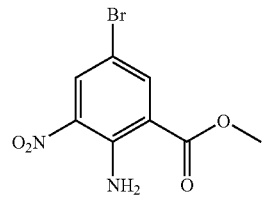

Methyl 2-amino-5-bromo-3-nitro benzoate: To a slurry of methyl 5-bromo-3-nitro-2N-trifluoroacetylamino benzoate (2.1 g, 5.66 mmol) in methanol (40 mL) was added hydrochloric acid (20 mL, 6N). The resulting mixture was heated at 75-80° C. for 12 hours then cooled to afford a yellow suspension which was filtered and washed with water. The collected solids were dried at 50° C. under reduced pressure to provide 1.1 g of the title compound as a bright yellow solid. $^1$H NMR (CDCl$_3$) δ 3.93 (s, 3H), 8.32 (d, 1H), 8.51 (d, 1H).

Example 3

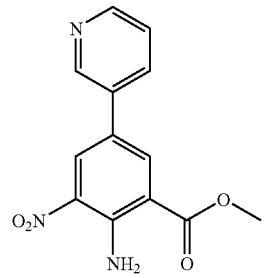

Methyl-2-amino-3-nitro-5-(3'-pyridyl) benzoate: To a nitrogen purged mixture of methyl 2-amino-5-bromo-3-nitro benzoate (0.3 g, 1.09 mmol) in ethylene glycol dimethyl ether (8 mL) was added sodium bicarbonate (1M, 2.18 mL, 2.18 mmol), 3-pyridyl boronic acid (0.201 g 1.636 mmol), and tetrakis triphenyphosphine palladium (0) (0.125 g, 0.11 mmol). The resulting mixture was refluxed for 12 hours, cooled, diluted with sodium bicarbonate (aqueous, saturated) and extracted in to ethyl acetate (3×). The combined organic layers were washed with brine, dried over sodium sulfate, filtered and concentrated under reduced pressure to afford a dark yellow solid. The crude product was purified by flash chromatography (Silica Gel, 30 to 100% hexanes/ethyl acetate) provide 0.069 g of the title compound as a yellow solid. HPLC $R_t$=1.76 minutes, MS (M+H=274)

Example 4

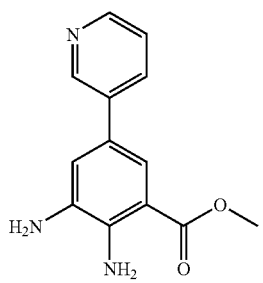

Methyl-2,3-diamino-5-(3'-pyridyl) benzoate: To a slurry of 10% Pd on carbon (0.035 g) in ethanol (10 mL) was added a slurry of methyl-2-amino-3-nitro-5-(3'-pyridyl) benzoate (0.167 g, 0.61 mmol) in ethanol (15 mL). The partial suspension was hydrogenated at 40 PSI for 6 hours. The catalyst was then removed by filtrated and the filtrated concentrated under reduced pressure to provided 0.11 g of the title compound as a light yellow solid. $^1$H NMR (CDCl$_3$) δ 3.54 (bs, 1H), 3.91 (s, 3H), 5.76 (bs, 1H), 7.08-7.81(m, 7H), 8.54 (m, 1H), 8.79 (m, 1H).

Example 5

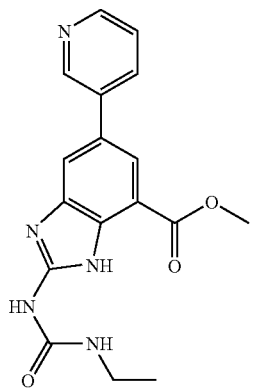

I-1

2-(3-Ethyl-ureido)-6-pyridin-3-yl-3H-benzoimidazole-4-carboxylic acid methyl ester (I-1): To a suspension of methyl-2,3-diamino-5,3'-pyridyl benzoate (0.109 g, 0.448 mmol) in water (1 mL) was added sulfuric acid (1N, 1.2 mL) and a solution of N'-ethyl-N-cyanourea (1M, 0.9 mL, 0.94 mmol)). The pH was adjusted with 1N sulfuric acid to 3-4 and the resulting reaction mixture heated at reflux for 12 hours. The reaction was cooled and the resulting suspension was filtered and washed with water. The collected solids purified by flash chromatography (Silica Gel, 100% methylene chloride to 100% (May 10, 1985 v/v/v NH4OH/MeOH/CH2Cl2) to provide a tan solid that was recrystallized from methanol and diethyl ether to provide 0.009 g of the title compound as an off white solid. HPLC $R_t$=1.5 minutes, MS (M+H=340), $^1$H NMR (DMSO) δ 1.13 (t, 3H), 3.24 (m, 2H), 3.97 (s, 3H), 7.48 (m, 2H), 7.91 (s, 1H), 8.03 (s, 1H), 8.14 (m, 1H), 8.56 (d, 1H), 8.92 (s, 1H) 9.92 (bs, 1H), 11.51 (bs, 1H).

Example 6

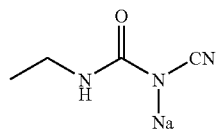

N'-Ethyl-N-cyanourea, sodium salt

Method A: To a 20° C. solution of sodium hydroxide (1.5 M aqueous, 50 mL, 75.02 mmol) was added cyanamide (8.5 g, 202.25 mmol) then ethyl isocyanate (4 mL, 50.56 mmol) was added in a dropwise fashion over 10 minutes. After stirring for 30 minutes, additional sodium hydroxide (3M, 25 mL. 75.02 mmol) and ethyl isocyanate (4 mL, 50.56 mmol) were added. The resulting solution was then aged for a minimum of 30 minutes before using directly without isolation.

Method B: A solution of sodium t-butoxide (124.1 g) in THF (500 mL, anhydrous) is prepared at ambient temperature then cooled via ice-bath. In a separate reaction vessel, a solution of cyanamide (51.76 g) in THF (300 mL, anhydrous) is combined with ethyl isocyanate (97.5 mL) and cooled via ice-bath. To the resulting cyanamide/isocyanate solution is added the sodium t-butoxide/THF solution at a rate sufficient to maintain the internal temperature less than 30° C. The resulting white solid is collected by filtration. The collected solid is then combined with THF (500 mL) and the resulting slurry stirred on ice-bath for 15 minutes. The white solid is collected via filtration and dried in vacuo to afford the 151.5 g of the title compound (91% yield). $R_t$ (min)=3.0 minutes.

Example 7

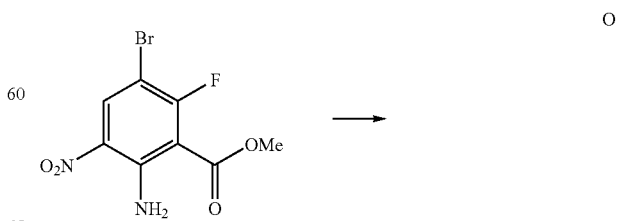

47

-continued

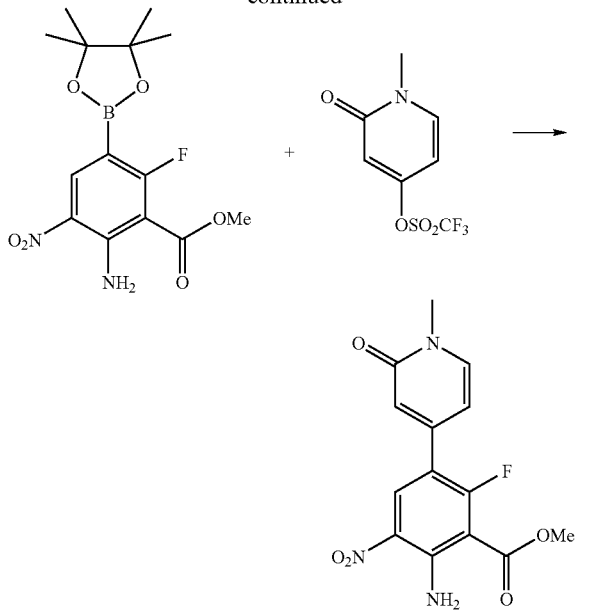

2-Amino-6-fluoro-5-(1-methyl-2-oxo-1,2-dihydro-pyridin-4-yl)-3-nitro-benzoic acid methyl ester: To a solution of 2-amino-5-bromo-6-fluoro-3-nitro-benzoic acid methyl ester (1.0 g, 3.4 mmol) in dioxane (25 mL), under nitrogen atmosphere, was added bispinacoladaboron (1.3 g, 5.1 mmol), dichloro[1,1'-bis(diphenylphosphine)ferrocene]palladium (II) dichlormethane adduct (0.125 g, 0.17 mmol), and potassium acetate (1.0 g, 10.2 mmol). The resulting mixture was heated at reflux for 18 hours, cooled to room temperature, diluted with ethyl acetate (50 ml) and filtered through Celite®. The resulting solid was triturated with hexanes (40 ml) three times to afford 0.515 g of 2-amino-6-fluoro-3-nitro-5-(4,4,5,5-tetramethyl-[1,3,2]dioxaborolan-2-yl)-benzoic acid methyl ester. To a mixture of 2-amino-6-fluoro-3-nitro-5-(4,4,5,5-tetramethyl-[1,3,2]dioxaborolan-2-yl)-benzoic acid methyl ester in ethylene glycol dimethyl ether (10 ml) was added trifluoro-methanesulfonic acid 1-methyl-2-oxo-1, 2-dihydro-pyridin-4-yl ester (0.39 g, 1.5 mmol), lithium chloride (0.25 g, 6.0 mmol), sodium carbonate (1.1 ml, 2.2 mmol of 2M), and tetrakistriphenylphosphine palladium (0.18 g, 0.15 mmol). The resulting mixture was heated to 90° C. and allowed to stir for 18 hours. After cooling and concentration in vacuo, the residue was purified by chromatography (Silica Gel 0.5% methanol/dichloromethane to 2% methanol/dichloromethane) to provide the title compound (0.275 g, 25%). $^1$H NMR (500 MHz, CDCl$_3$) δ 3.58 (s, 3H), 4.03 (s, 3H), 6.30 (d, 1H), 7.32 (d, 1H), 8.45 (br s, 2H), 8.53 (d, 1H)

Example 8

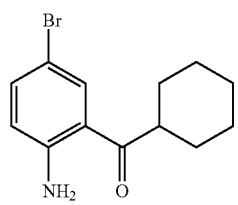

(2-Amino-5-bromo-phenyl)-cyclohexyl-methanone: To a suspension of 2-amino-5-bromo-benzonitrile (2.13 g, 10.80 mmol) in dry THF (20 mL) cooled to 0° C. was added cyclohexyllmagnesium bromide (1N in THY, 37.8 mL, 37.8 mmol,

48

3.5 equivalents) in a dropwise fashion. The resulting yellow reaction mixture was warmed to room temperature and stirred for 20 hours. The reaction was then cooled to 0° C., slowly quenched with saturated aqueous ammonium chloride (30 mL), and diluted with water (30 mL) and EtOAc (50 mL). The biphasic mixture was vigorously stirred until all solids formed dissolved. The phases were separated and the aqueous layer extracted with EtOAc (25 mL). The combined organic extracts were washed with brine, dried (MgSO$_4$), filtered and the filtrate concentrated in vacuo. The crude product was purified by flash chromatography (SiO$_2$, hexanes to 19:1 hexanes:EtOAc) to give 2.43 g (80%) of the title compound as a yellow solid: $^1$H NMR (CDCl$_3$, 500 MHz) δ 7.84 (d, 1H), 7.35 (dd, 1H), 6.72 (d, 1H), 3.18 (m, 1H), 1.86 (m, 4H), 1.74 (m, 1H), 1.39-1.53 (m, 4H), 1.25 (m, 1H); MS (ES+) m/z (M$^+$+1) 282.07.

Example 9

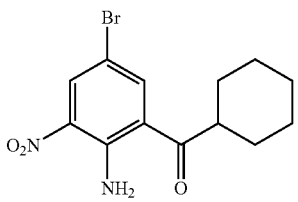

(2-Amino-5-bromo-3-nitro-phenyl)-cyclohexyl-methanone: A suspension of (2-amino-5-bromo-phenyl)-cyclohexyl-methanone (2.40 g, 8.50 mmol) in acetic anhydride (40 mL) was heated at 80° C. for 1 hour. The reaction mixture was concentrated to dryness then dissolved in fuming nitric acid (18 mL). The resulting yellow solution was stirred at room temperature for 2 hours. The resulting light orange solution was poured into ice and a yellow precipitate formed. The reaction mixture was stirred until all the ice melted and filtered to give a pale yellow solid. This solid was dissolved in EtOH (10 mL) and 6N aqueous hydrochloric acid (20 mL). The solution was stirred at 80° C. for 3 hours, cooled to room temperature, diluted with water (20 mL), and basified with sodium carbonate (1 g). The resulting mixture was diluted with hexanes (50 mL) and the biphasic mixture was stirred until all solids dissolved. The phases were separated and the aqueous layer was extracted with hexanes (2×25 mL). The combined organic extracts were washed with water, dried (MgSO$_4$), filtered and the filtrate concentrated in vacuo to afford the title compound (1.17 g, 43% yield) as a yellow solid: $^1$H NMR (CDCl$_3$, 500 MHz) δ 8.50 (s, 1H), 8.12 (s, 1H), 3.20 (m, 1H), 1.86 (m, 4H), 1.74 (m, 1H), 1.51 (m, 2H), 1.39 (m, 2H), 1.27 (m, 1H).

Example 10

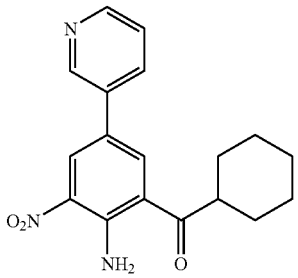

(2-Amino-3-nitro-5-pyridin-3-yl-phenyl)-cyclohexyl-methanone: To a solution of (2-amino-5-bromo-3-nitro-phenyl)-cyclohexyl-methanone (600 mg, 1.83 mmol) in DME (25 mL) was added, successively, pyridine-3-boronic acid 1,3-propanediol cyclic ester (388 mg, 2.38 mmol), (tetrakistriphenylphosphine) palladium(0) (212 mg, 0.18 mmol), and 1N NaHCO$_3$ (3.7 mL, 3.7 mmol). The resulting mixture was stared at 90° C. for 90 minutes then cooled to room temperature. The reaction mixture was diluted with EtOAc (100 mL), washed with water (50 mL), brine (50 mL), dried (MgSO$_4$), filtered and the filtrate concentrated in vacuo. The resulting residue was purified by flash chromatography (SiO$_2$, hexanes to 3:1 hexanes:EtOAc) to afford 527 mg (89%) of the title compound as a pale orange solid: $^1$H NMR (CDCl$_3$, 500 MHz) δ 8.92 (d, 1H), 8.69 (d, 1H), 8.66 (d, 1H), 8.31 (d, 1H), 8.20 (d, 1H), 7.71 (dd, 1H), 3.36 (m, 1H), 1.88 (m, 3H), 1.77 (m, 1H), 1.40-1.61 (m, 3H), 1.24-1.32 (m, 2H), 0.89 (m, 1H).

Example 11

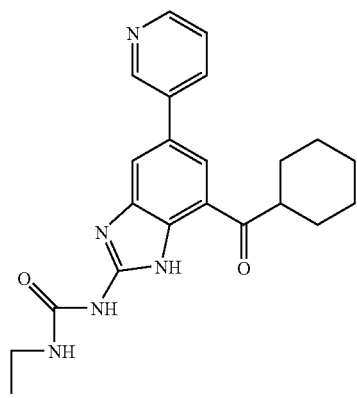

I-14

1-(7-Cyclohexanecarbonyl-5-pyridin-3-yl-1H-benzoimidazol-2-yl)-3-ethyl-urea (I-14): A suspension of 4 (42 mg, 0.13 mmol) and tin(II) chloride dihydrate (87 mg, 0.39 mmol) in EtOH (4 mL) was heated at reflux for 4 hours. The mixture was cooled to room temperature, basified with saturated aqueous NaHCO$_3$ (10 mL), and diluted with EtOAc (15 mL). Celite (10 g) was added and the resulting suspension was stirred (30 minutes), filtered over a path of celite and the filtrate concentrated in vacuo. The resulting residue was diluted with water (5 mL), and 1N aqueous N'-ethyl-N-cyanourea was added. Enough 1N aqueous sulfuric acid was added dropwise to achieve pH 3. The resulting mixture was heated at 100° C. for 16 hours. The reaction mixture was then cooled to ambient temperature, basified with saturated aqueous NaHCO$_3$, and diluted with EtOAc. The phases were separated and the organic layer was dried (MgSO$_4$), filtered, and the filtrate concentrated in vacuo. The residue was purified by preparative HPLC to afford 8 mg of the title compound as the bis-TFA salt which was converted to the bis-HCl salt to afford 7 as a pale yellow solid: HPLC: R$_t$=4.52 minutes; $^1$H NMR (CD$_3$OD, 500 MHz) δ 9.40 (s, 1H), 9.08 (d, 1H), 8.95 (d, 1H), 8.48 (s, 1H), 8.27 (m, 2H), 3.72 (m, 1H), 3.36 (q, 2H), 1.99 (m, 2H), 1.86 (m, 2H), 1.83 (m, 1H), 1.57 (m, 4H), 1.32 (m, 1H), 1.23 (t, 3H); MS (ES$^+$) m/z (M$^+$+1) 392.2.

Example 12

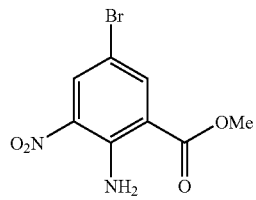

2-Amino-5-bromo-3-nitro-benzoic acid methyl ester: To a solution of 2.23 g (10.4 mmol) of 2-amino-3-nitro-benzoic acid methyl ester in 12 mL of acetic acid was added dropwise over 5 minutes a solution of 0.53 mL (10.4 mmol, 1 eq) of bromine in 2 mL of acetic acid. The mixture was stirred at room temperature for 30 minutes and poured into 100 grams of ice. The precipitated yellow solid was collected by suction filtration and dried to afford 2.50 g (82%) of the title compound as a yellow solid. $^1$H NMR (CDCl$_3$) δ 3.95 (s, 3H), 8.35 (br s, 2H), 8.6 (d, 1H).

Example 13

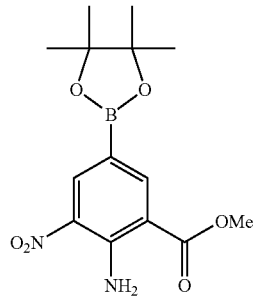

2-Amino-3-nitro-5-(4,4,5,5-tetramethyl-[1,3,2]dioxaborolan-2-yl)-benzoic acid methyl ester: To a solution of 2-amino-5-bromo-3-nitro-benzoic acid methyl ester, (0.5 g, 1.82 mmol) in dioxane (5 mL) was added bispinacoladaboron (0.554 g, 2.18 mmol), dichloro[1,1'-bis(diphenylphosphine)ferrocene]palladium (II) dichlormethane adduct (0.133 g, 0.18 mmol), and potassium acetate (0.535 g, 5.45 mmol). The resulting mixture was refluxed for 3 hours. After cooling and concentration in vacuo the dark solid was purified (SiO$_2$, CH$_2$Cl$_2$ to 50% ethyl acetate in CH$_2$Cl$_2$) to provide the title compound as an orange solid (0.347 g, 57%). $^1$H NMR (500 MHz, CDCl$_3$) δ 1.32 (s, 6H), 3.91 (s, 3H), 8.3 (bs, 1H), 8.59 (s, 1H), 8.8 (s, 1H), 8.99 (bs, 1H).

Example 14

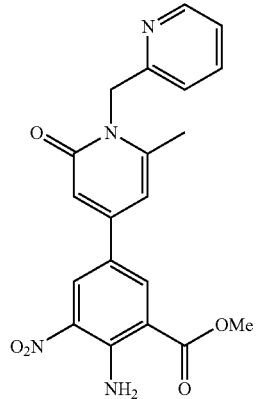

2-Amino-5-(5-methyl-3-oxo-4-pyridin-2-ylmethyl-cyclo-hexa-1,5-dienyl)-3-nitro-benzoic acid methyl ester: To a solution of 2-amino-3-nitro-5-(4,4,5,5-tetramethyl-[1,3,2]di-oxaborolan-2-yl)-benzoic acid methyl ester (0.163 g, 0.51 mmol) in ethylene glycol dimethylether (5 mL) was added N-(methyl-2-pyridinyl)-6-methyl-4-trifluoromethylsulfony-loxy-2-pyridone (0.136 g, 0.41 mmol), bis(triph-enylphoshine)palladium (II) dichloride (0.029 g, 0.04 mmol), and sodium carbonate (0.62 mL, 1.24 mmol of 2M). The resulting mixture was heated at reflux for 3 hours. After cooling and concentration in vacuo the resulting dark solid was purified (SiO$_2$, 50% ethyl acetate/methylene chloride to 3% methanol in 50% ethyl acetate/methylene chloride) to provide the title compound as an orange solid (0.176 g, 89%). $^1$H NMR (500 MHz, CDCl$_3$) δ 2.41 (s, 3H), 3.39 (s, 3H), 5.5 (s, 2H), 6.28 (s, 1H), 6.68 (s, 1H), 7.3-7.1 (m, 2H), 7.62 (t, 1H), 8.49 (s, 1H), 8.61 (s, 1H).

Example 15

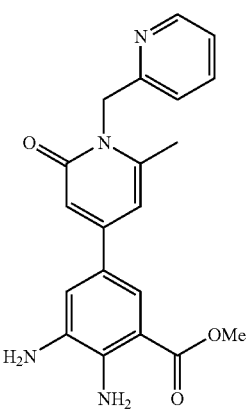

2,3-Diamino-5-(5-methyl-3-oxo-4-pyridin-2-ylmethyl-cyclohexa-1,5-dienyl)-benzoic acid methyl ester: To a slurry of 10% palladium on carbon (0.045 g) in ethyl acetate (20 mL) was added 2-amino-5-(5-methyl-3-oxo-4-pyridin-2-yl-methyl-cyclohexa-1,5-dienyl)-3-nitro-benzoic acid methyl ester (0.176 g, 0.44 mmol). The resulting mixture was hydrogenated at 30 psi for 24 hours. The reaction was filtered, concentrated in vacuo, and the crude isolate purified (SiO$_2$, 2 to 10% methanol in methylene chloride) to afford the title compound. $^1$H NMR (500 MHz, CDCl$_3$) δ 2.5 (s, 3H), 3.99 (s, 3H), 5.3 (s, 2H), 5.38 (bs, 2H), 6.39 (s, 1H), 6.25 (s, 1H), 7.93-7.21 (m, 4H), 8.61 (s, 1H), 8.93 (s, 1H).

Example 16

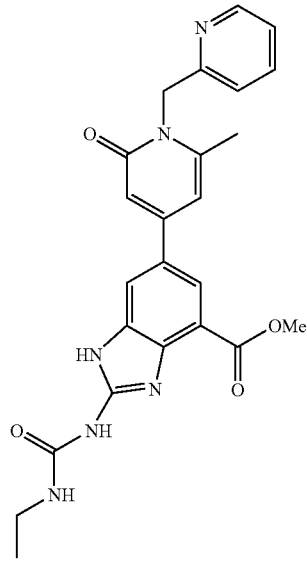

I-32

2-(3-Ethyl-ureido)-6-(5-methyl-3-oxo-4-pyridin-2-ylm-ethyl-cyclohexa-1,5-dienyl)-1H-benzoimidazole-4-car-boxylic acid methyl ester (1-32): To a mixture of 2,3-di-amino-5-(5-methyl-3-oxo-4-pyridin-2-ylmethyl-cyclohexa-1,5-dienyl)-benzoic acid methyl ester (0.084 g, 0.23 mmol) in 20% aqueous dimethylsulfoxide (5 mL) was added sulfuric acid (0.5 mL) and N'-ethyl-N-cyanourea (0.58 mL at 1M in NaOH, 0.58 mmol). After adjusting the pH to ~3 with additional sulfuric acid the resulting mixture was heated to reflux for 3 hours. After cooling to room temperature the mixture was basified with saturated aqueous sodium carbonate and diluted with water. The resulting suspension was filtered and further washed with water. The solids were dissolved in tetrahydrofuran, dried over sodium sulfate, filtered and concentrated to dryness. The aqueous mother liquor was extracted with ethyl acetate, washed with brine, dried over sodium sulfate, filtered and dried in vacuo. The free base isolated from the mother liquors was taken up in ethyl acetate and methanol, acidified with excess anhydrous HCl and concentrated to dryness to provide the title compound as the dihydrochloride salt (tan solid, 0.036 g). $^1$H NMR (500 MHz, DMSO) δ 1.12 (t, 3H), 2.41 (s, 3H), 3.22 (m, 2H), 3.97 (s, 3H), 5.38 (s, 2H), 6.6 (s, 1H), 6.68 (s, 1H), 7.8-7.25 (m, 2H), 7.48 (bs, 1H), 7.79 (t, 1H), 7.94 (s, 1H), 8.03 (s, 1H), 8.49 (s, 1H), 9.93 (bs, 1H), 11.53 (bs, 1H). HPLC: R$_t$=3.7 minutes [10 to 90% 12 minutes gradient @1 ml/min 0.1% TFA (YMC 3×150)]. MS: M+H=461, M−H=459. MS/HPLC R$_t$=2.24 minutes.

Example 17

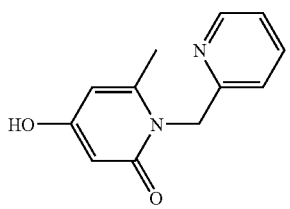

4-Hydroxy-6-methyl-1-pyridin-2-ylmethyl-1H-pyridin-2-one: To a suspension of 12.6 g (0.1 mol) of 4-hydroxy-6-methyl-2-pyrone in 50 ml water was added 2-(aminomethyl)pyridine (10.3 ml, 0.1 mol) and the mixture heated to reflux for 2.5 hours. The resulting light yellow compound was filtered from the cooled mixture. Concentration of the filtrate and trituration of the resulting gum with dichloromethane afforded a second crop of the title compound (19.85 g, 92%). NMR (DMSO-d6, ppm): 10.5 (s, 1H), 8.5 (d, 1H), 7.7-7.8 (t, 1H), 7.2 (t, 1H), 7.1 (d, 1H), 5.8 (s, 1H), 5.5 (s, 1H), 5.2 (s, 2H), 2.2 (s, 3H). FIA: m/z-215.1 ES−/217.1 ES+

Example 18

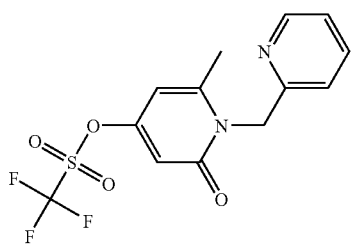

Trifluoro-methanesulfonic acid 6-methyl-2-oxo-1-pyridin-2-ylmethyl-1,2-dihydro-pyridin-4-yl ester: To a suspension of N-(methyl-2-pyridinyl)-4-hydroxy-6-methyl-2-pyridone (10.0 g, 0.046 mol) in dimethylformamide (70 mL) was added N-phenyltrifluoromethylsulfonimide (18.2 g, 0.05 mol) followed by triethylamine (7.7 ml, 0.055 mol) and the mixture stirred overnight at room temperature. The reaction mixture was poured into 400 ml water and extracted with ethyl acetate (4×100 ml). The combined extracts were washed with 2N NaOH (2×200 ml), water (4×200 ml) and saturated brine (1×150 ml) before drying and concentration. Filtration through a 2 inch plug of silica gel with hexanes as eluent (discarded) and then a 50% mixture of ethyl acetate/hexanes and concentration of the filtrate afforded the title compound as a white solid (12.8 g, 80%). $^1$H NMR: (CDCl$_3$, ppm): 8.5 (d, 1H), 7.7 (t, 1H), 7.3 (d, 1H), 7.2 (m, 1H), 6.4 (s, 1H), 6.1 (s, 1H), 5.4 (s, 2H), 2.5 (s, 3H). FIA: m/z-349.0 ES+.

Example 19

I-40

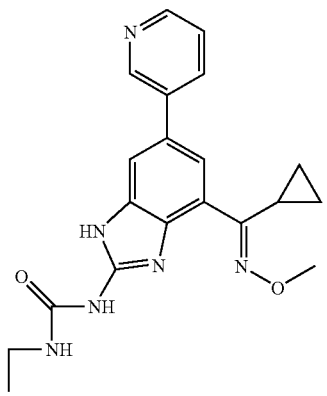

1-[4-(Cyclopropyl-methoxyimino-methyl)-6-pyridin-3-yl-1H-benzoimidazol-2-yl-3-ethyl-urea (1-40): To a solution of 1-(4-cyclopropanecarbonyl-6-pyridin-3-yl-1H-benzoimidazol-2-yl)-3-ethyl-urea (37.2 g, 0.106 mmol) in dry EtOH (3 mL) were added potassium acetate (84 mg, 0.848 mmol, 8 eq.), methoxylamine hydrochloride (70.8 mg, 0.848 mmol, 8 eq.), molecular sieves (4A, powdered) in succession. The resulting suspension was stirred at 50° C. for 36 hours. The reaction mixture was then cooled to ambient temperature, diluted with EtOAc and water. The phases were separated, the aqueous layer was extracted with EtOAc (1×) and the combined organic extracts were dried (MgSO$_4$), filtered, and the filtrate concentrated in vacuo. The residue was purified by preparative HPLC, converted to the bis-HCl salt to afford the title compound as a tan solid (11.0 mg): HPLC (10 to 90% CH$_3$CN, 8 min.): t$_R$=4.05 minutes; $^1$H NMR (CD$_3$OD, 500 MHz) δ 9.30 (s, 1H), 8.99 (d, 1H), 8.90 (d, 1H), 8.22 (dd, 1H), 8.18 (s, 1H), 8.04 (s, 1H), 4.14 (s, 3H), 3.36 (q, 2H), 2.04 (m, 1H), 1.23 (t, 3H), 1.15 (m, 2H), 0.92 (m, 2H); MS (ES+) m/z (M$^+$+1) 379.2.

Example 20

I-44

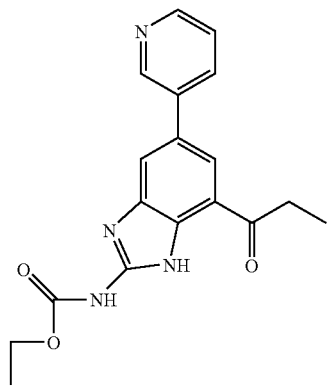

(7-Propionyl-5-pyridin-3-yl-1H-benzoimidazol-2-yl)-carbamic acid ethyl ester (1-44): To a mixture of 2-methyl-2-thiopseudourea (109 mg, 0.39 mmol) and ethyl chloroformate (75 μL, 0.78 mmol) in water (2 mL) at 5° C. was added over 40 minutes a 6N aqueous NaOH solution until pH stabilized to 8. The pH was then adjusted to 5 with glacial AcOH. A suspension of 1-(2,3-diamino-5-pyridin-3-yl-phenyl)-propan-1-one (0.30 mmol) in water (5 mL) was subsequently added to the reaction mixture. The reaction was heated at 90° C. for 18 hours, cooled to ambient temperature, and diluted with water (10 mL) and EtOAc (20 mL). The phases were separated and the aqueous layer extracted with EtOAc (3×). The combined organic extracts were washed with brine, dried (MgSO$_4$), filtered, and the filtrate concentrated in vacuo. The crude residue was taken up in DMSO, purified by preparative HPLC, and by flash column chromatography (SiO$_2$; CH$_2$Cl$_2$: MeOH, 1:0 to 19:1). The residue was then converted to the bis-HCl salt to afford the title compound as an off white solid (5.0 mg): HPLC (10 to 90% CH$_3$CN, 8 min.): R$_t$=3.90 minutes; $^1$H NMR (CD$_3$OD, 500 MHz) δ 9.39 (d, 1H), 9.07 (d, 1H), 8.93 (d, 1H), 8.48 (d, 1H), 8.28 (d, 1H), 8.25 (dd, 1H), 4.46 (q, 2H), 3.35 (q, 2H), 1.43 (t, 3H), 1.29 (t, 3H); MS (ES+) m/z (M$^+$+1) 339.1.

Example 21

The following compounds set forth in Table 2 below were prepared according to methods known in the art, General Schemes I through IX, and by methods substantially similar to those set forth in Examples 1-20 above. The characterization data for these compounds is summarized in Table 2 below and includes $^1$H NMR (at 500 MHz) and mass spectral (MS) data. Compound numbers correspond to the compound numbers listed in Table 1

TABLE 2

Characterization Data for Selected Compounds of Formula I

| No. I- | M − 1 | M + 1 | $^1$H-NMR |
|---|---|---|---|
| 4 | 365.18 | 367.16 | — |
| 11 | 390.2 | 392.2 | (CD$_3$OD) 9.40(s, 1 H), 9.08(d, 1 H), 8.95(d, 1 H), 8.48(s, 1 H), 8.27(m, 2 H), 3.72(m, 1 H), 3.36(q, 2 H), 1.99(m, 2 H), 1.86(m, 2 H), 1.83(m, 1 H), 1.57(m, 4 H), 1.32(m, 1 H), 1.23(t, 3 H) |
| 17 | 413 | 415 | (CD$_3$OD) 1.18(t, 3 H), 3.3(m, 2 H), 4.73(s, 2 H), 7.27-7.42(m, 3 H), 8.0(s, 2 H), 8.28(s, 1 H), 8.75(s, 1 H), 9.12(s, 1 H). |
| 18 | 322 | 324.1 | (dmso-d6): 11.77(1 H, s); 9.86(1 H, s); 9.02(1 H, d); 8.59(1 H, d); 8.22(1 H, dd); 8.07(1 H, d); 8.03(1 H, s); 7.51(2 H, m); 3.26(2 H, dq); 2.77(3 H, s); 1.12(3 H, t). |
| 19 | 338.14 | 1.8 | (CD$_3$OD): 9.38(s, 1 H), 9.06(d, 1 H), 8.94(d, 1 H), 8.48(s, 1 H), 8.26(m, 2 H), 3.49(q, 2 H), 3.38(q, 2 H), 1.29(t, 3 H), 1.24(t, 3 H). |
| 20 | 352 | 2.06 | (CD$_3$OD) 1.06(t, 3 H), 2.22(t, 3 H), 3.2(m, 2 H), 3.36(m, 2 H), 7.57(m, 1 H), 7.92(s, 1 H), 8.03(s, 1 H) 8.19(d, 1 H), 8.53(d, 1 H), 8.89(s, 1 H). |
| 21 | 366.1 | 2.26 | (CD$_3$OD) 9.35(s, 1 H), 9.03(d, 1 H), 8.92(d, 1 H), 8.47(s, 1 H), 8.21-8.26(m, 2 H), 3.81-3.84(m, 1 H), 3.37(q, 2 H), 1.89-1.94(m, 1 H), 1.59-1.63(m, 1 H), 1.30(d, 3 H), 1.24(t, 3 H), 0.98(t, 3 H) |
| 22 | 352 | 1.9 | (CD$_3$OD) d 1.23(t, 3 H), 1.31(d, 2 H), 3.48(q, 2 H), 3.96(m, 1 H), 8.34(m, 2 H), 8.49(s, 1 H), 8.92(d, 1 H), 9.04(d, 1 H), 9.47(s, 1 H). |
| 23 | 337 | 339.2 | (CD$_3$CN) 12.55(br s, 1 H), 12.50(br s, 1 H), 9.30(s, 1 H), 9.25(s, 2 H), 8.29(s, 1 H), 8.14(s, 1 H), 6.86(m, 1 H), 3.32(m, 2 H), 3.25(q, 2 H), 1.25(t, 3 H), 1.18(t, 3 H) |
| 25 | — | 350.1 | (CD$_3$OD) 9.43(br s, 1 H), 9.09(br s, 1 H), 8.94(br s, 1 H), 8.68(br s, 1 H), 8.29(s, 1 H), 8.24(br s, 1 H), 3.36(q, 2 H), 3.22(m, 1 H), 1.30(br s, 2 H), 1.23(m, 5 H) |
| 26 | 388.12 | 390.2 | (dmso-d6) 1.1(t, 3 H), 3.25(m, 2 H), 4.1(s, 3 H), 7.3(s, 1 H), 7.5(m, 1 H), 7.7(s, 1 H), 7.75(m, 1 H), 8.1(s, 1 H), 8.3(m, 1 H), 8.7(mm, 1 H), 8.9(m, 1 H), 9.05(s, 1 H), 10.1(br s, 1 H) |
| 27 | 455.97 | 458.04 | (CD$_3$OD) 8.9(m, 2 H), 8.6(m, 2 H), 8.1(m, 2 H), 6.6(s, 1 H), 6.8-6.9(d, 1 H) 5.85(s, 2 H), 5.7-5.8(3 H – NH+), 3.6(q, 2 H), 3.35(s, 3 H), 3.2(q, 2 H), 1.2(t, 3 H), 1.1(t, 3 H) |
| 28 | 376 | 378 | (CD$_3$OD) d 1.2(m, 3 H), 1.75(m, 3 H), 2.12-1.93(m, 3 H), 3.39(q, 2 H), 4.12(m, 1 H), 8.12(t, 1 H), 8.18(s, 1 H), 8.49(s, 1 H), 8.87(d, 1 H), 8.9(d, 1 H), 9.26(s, 1 H). |
| 29 | 404.15 | 2.81 | (dmso d6) 1.1(t, 3 H), 1.45(t, 3 H), 3.3(m, 2 H), 4.5(q, 2 H), 7.3(s, 1 H), 7.55(br s, 1 H), 7.75(m, 1 H), 7.8(s, 1 H), 8.1(s, 1 H), 8.4(m, 1 H), 8.7(m, 1 H), 8.9(br s, 1 H), 9.05(s, 1 H), 10.2(br s, 1 H) |
| 30 | 390.22 | 2.13 | (dmso-d6) 1.1(t, 3 H), 3.2(m, 2 H), 3.8(s, 3 H), 7.6(m, 1 H), 7.8(m, 1 H), 8.05(s, 1 H), 8.2(s, 1 H), 8.3(s, 1 H), 8.45(m, 1 H), 8.7(m, 1 H), 8.8(s, 1 H), 9.1(s, 1 H), 10.3(br s, 1 H) |
| 31 | 415.22 | 1.84 | (dmso-d6) 1.1(t, 3 H), 3.2(m, 2 H), 3.3(t, 2 H), 3.9(t, 2 H), 7.4(m, 1 H), 7.55(m, 1 H), 7.7(m, 1 H), 7.8(m, 1 H), 8.0(s, 1 H), 8.15(s, 1 H), 8.2(m, 1 H), 8.4(m, 1 H), 8.7(m, 2 H), 9.1(s, 1 H), 10.1(br s, 1 H) |
| 33 | 366 | 368 | (DMSO-d6) d 1.1(t, 3 H), 1.5(d, 6 H), 3.25(m, 2 H), 5.25(m, 1 H), 7.38(bs, 1 H), 7.5(m, 1 H), 7.88(s, 1 H), 8.0(s, 1 H), 8.1(d, 1 H), 8.56(d, 1 H), 8.91(s, 1 H), 10.12(bs, 1 H), 11.51(bs, 1 H)> |
| 34 | 352 | 354 | (DMSO-d6) d 1.11(t, 3 H), 1.42(t, 3 H), 3.21(m, 2 H), 4.41(m, 2 H), 7.5(m, 1 H), 7.89(s, 1 H), 8.03(s, 1 H), 8.12(d, 1 H), 8.93(s, 1 H), 10.09(bs, 1 H), 1.55(bs, 1 H). |
| 35 | 386.2 | 388.2 | (DMSO-d6/CD$_3$OD) 1.21(t, 3 H) 3.30(q, 2 H) 3.59(s, 3 H) 4.05(s, 3 H) 6.50(d, 1 H) 6.65(s, 1 H) 7.73(d, 1 H) 7.88(d, 1 H) |
| 36 | 385.2 | 387.3 | (CD$_3$OD), 1.22(t, 3 H) 3.01(s, 3 H) 3.32(q, 2 H) 3.71(s, 3 H) 6.80(d, 1 H) 6.96(s, 1 H) 7.85(d, 1 H), 7.95(d, 2 H) |
| 37 | 380 | 382 | — |
| 38 | — | 367.2 | (CD$_3$OD) 8.80-8.87(br s, 1 H), 8.45-8.55(br m, 1 H), 8.13(d, 1 H), 8.10(m, 1 h minor isomer), 7.71(s, 1 H), 7.59(s, 1 H), 7.52-7.55(m, 1 H), 7.36(s, 1 H minor isomer), 4.15(s, 3 H), 3.89(s, 3 H minor isomer), 3.34(q, 2 H), |
| 41 | 391.1 | 393.2 | (DMSO-d6) 10.8(br s, 1 H), 9.13(s, 1 H), 8.77(d, 1 H), 8.58(br s, 1 H), 7.90(m, 2 H), 7.75(br s, 1 H), 7.55(br s, 1 H), 4.27(q, 2 H), 3.23(m, 2 H), 2.20(m, 1 H), 1.32(t, 3 H), 1.14(t, 3 H), 0.94(br d, 2 H), 0.65(br s, 2 H) |
| 42 | — | 391 | (CD$_3$OD) 1.23(t, 3 H), 2.28-1.67(m, 8 H), 3.45(q, 2 H), 3.75(m, 1 H, major), 4.11(m, 1 H, minor), 8.30-7.82(m, 3 H), 8.65(m, 2 H), 9.10(s, 1 H, major), 9.18(s, 1 H, minor). |
| 43 | — | 392 | (CD$_3$OD) 1.22(t, 3 H), 2.20-1.65(m, 8 H), 3.35(q, 2 H), 3.72(m, 1 H, minor), 4.11(m, 1 H, major), 8.32-7.88(m, 3 H), 8.78(m, 2 H), 9.18(s, 1 H, minor), 9.20(s, 1 H, major). |
| 44 | 422.2 | 424.1 | (dmso-d6): 9.81(s, 1 H); 9.26(s, 1 H); 8.84(dd, 1 H); 8.29(d, 1 H); 8.14(d, 1 H); 8.12(d, 1 H); 7.47(d, 1 H); 7.28(d, 1 H); 6.12(s, 1 h); 3.34(s, 6 H); 3.33(dq, 2 H); 2.82(m, 1 H); 1.14(t, 3 H); 0.67(m, 2 H); 0.62(m, 2 H). |

Example 22

Gyrase ATPase Assay

The ATP hydrolysis activity of DNA gyrase was measured by coupling the production of ADP through pyruvate kinase/lactate dehydrogenase to the oxidation of NADH. This method has been described previously (Tamura and Gellert, 1990, *J. Biol. Chem.*, 265, 21342).

ATPase assays are carried out at 30° C. in buffered solutions containing 100 μM TRIS pH 7.6, 1.5 μM MgCl$_2$, 150 μM KCl. The coupling system contains (final concentrations) 2.5 μM phosphoenol pyruvate, 200 μM nicotinamide adenine dinucleotide (NADH), 1 μM DTT, 30 μg/ml pyruvate kinase, and 10 ug/ml lactate dehydrogenase. 40 nanomolar enzyme (374 kDa Gyr A2B2 subunit from *Staphylococcus aureus*) and a DMSO solution of the inhibitor to a final concentration of 4% are added and the reaction mixture is allowed to incubate for 10 minutes at 30° C. The reaction is then started by the addition of ATP to a final concentration of 0.9 μM and the rate of NADH disappearance at 340 nanometers is measured over the course of 10 minutes. The $K_i$ values are determined from rate versus concentration profiles and are reported as the average of duplicate values.

Compounds set forth in Table 1 supra were found to be inhibitors of gyrase.

Example 23

Topo IV ATPase Assay

The conversion of ATP to ADP by Topo4 enzyme is coupled to the conversion of NADH to NAD+ and measured by the change in absorbance at 340 nm. Topo4 is incubated with inhibitor (4% DMSO final) in buffer for 10 minutes at 30° C. Reaction is initiated with ATP and rates are monitored continuously for 20 minutes at 30° C. on a Molecular Devices SpectraMAX plate reader. The inhibition constant, Ki, is determined from plots of rate vs. [Inhibitor] fit to the Morrison Equation for tight binding inhibitors.

S. aureus Topo4 Buffer:
100 mM Tris 7.5, 2 mM $MgCl_2$, 200 mM K·Glutamate, 2.5 mM phosphoenol pyruvate, 0.2 mM NADH, 1 mM DTT, 4.25 µg/mL linearized DNA, 50 µg/mL BSA, 30 µg/mL pyruvate kinase, and 10 µg/mL lactate dehyrodgenase (LDH).

E. coli Topo4 Buffer:
100 mM Tris 7.5, 6 mM $MgCl_2$, 20 mM KCl, 2.5 mM phosphoenol pyruvate, 0.2 mM NADH, 10 mM DTT, 5.25 µg/mL linearized DNA, 50 µg/mL BSA, 30 µg/mL pyruvate kinase, and 10 µg/mL lactate dehyrodgenase (LDH).

Compounds set forth in Table 1 supra were found to be inhibitors of Topo IV.

Example 24

Susceptibility Testing in Liquid Media

Compounds of this invention were tested for antimicrobial activity by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing.

Several discrete bacterial colonies (3 to 7) from a freshly streaked plate were transferred to an appropriate rich broth medium such as MHB, supplemented where appropriate for the more fastidious organisms. This was grown overnight to high density followed by a 1 or 2-thousand-fold dilution to give an inoculation density of between $5\times10^5$ and $5\times10^6$ CFU per mL. Alternatively, the freshly picked colonies can be incubated at 37° C. for about 4 to 8 hours until the culture equals or exceeds a turbidity of a 0.5 McFarland standard (approximately $1.5\times10^8$ cellsper mL) and diluted to give the same CFU per mL as above. In a more convenient method, the inoculum was prepared using a commercially available mechanical device (the BBL PROMPT System) that involves touching five colonies directly with a wand, containing cross-hatch grooves at its bottom, followed by suspension of the bacteria in an appropriate volume of saline. Dilution to the appropriate inoculum cell density was made from this cell suspension. The broth used for testing consists of MHB supplemented with 50 mg per L of $Ca^{2+}$ and 25 mg per L of $Mg^{2+}$. Standard dilution panels of control antibiotics were made and stored as in the NCCLS standard M7-A5, the dilution range typically being in the 128 µg per mL to 0.015 µg per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately $5\times10^4$ CFU per well and the final volume was 100 µL. The plates were incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested does not grow. Such determinations were also compared to the appropriate tables contained in the above two publications to ensure that the range of antibacterial activity is within the acceptable range for this standardized assay.

Table 3 shows the results of the MIC assay for selected compounds of this invention tested against S. aureus. The compound numbers correspond to the compound numbers in Table 1. Compounds having an activity level designated as "A" provided an MIC of less than, or equal to, 0.5 µg/mL; compounds having an activity level designated as "B" provided an MIC of between 0.5 and 1.0 µg/mL; compounds having an activity level designated as "C" provided an MIC of greater than 1.0 µg/mL.

TABLE 3

MIC Values of Selected Compounds of Formula I Against S. aureus

| Compound No. | Activity | Compound No. | Activity |
| --- | --- | --- | --- |
| I-1 | A | I-3 | A |
| I-5 | A | I-6 | B |
| I-7 | C | I-11 | A |
| I-13 | C | I-14 | C |
| I-15 | C | I-16 | C |
| I-17 | B | I-18 | A |
| I-19 | A | I-20 | A |
| I-21 | A | I-22 | A |
| I-23 | A | I-24 | A |
| I-25 | A | I-26 | A |
| I-28 | A | I-29 | A |
| I-30 | C | I-31 | A |
| I-32 | A | I-33 | A |
| I-34 | A | I-35 | A |
| I-36 | C | I-37 | B |
| I-38 | A | I-39 | A |
| I-40 | A | I-41 | A |
| I-42 | A | I-43 | A |
| I-44 | C | — | — |

Table 4 shows the results of the MIC assay for selected compounds of this invention tested against S. pneumoniae. The compound numbers correspond to the compound numbers in Table 1. Compounds having an activity level designated as "A" provided an MIC of less than, or equal to, 0.5 µg/mL; compounds having an activity level designated as "B" provided an MIC of between 0.5 and 1.0 µg/mL; compounds having an activity level designated as "C" provided an MIC of greater than 1.0 µg/mL.

TABLE 4

MIC Values of Selected Compounds of Formula I Against S. pneumoniae

| No. | Activity | No.- | Activity |
| --- | --- | --- | --- |
| I-1 | A | I-4 | C |
| I-5 | A | I-11 | A |
| I-17 | A | I-18 | A |
| I-19 | A | I-20 | A |
| I-21 | A | I-22 | A |
| I-23 | A | I-24 | A |

TABLE 4-continued

MIC Values of Selected Compounds of Formula I Against *S. pneumoniae*

| No. | Activity | No.- | Activity |
|-----|----------|------|----------|
| I-25 | A | I-26 | A |
| I-28 | A | I-29 | A |
| I-30 | A | I-31 | A |
| I-32 | A | I-33 | A |
| I-34 | A | I-35 | A |
| I-36 | A | I-37 | A |
| I-38 | A | I-39 | A |
| I-40 | A | I-41 | A |
| I-42 | A | I-43 | A |
| I-44 | A | — | — |

While we have described a number of embodiments of this invention, it is apparent that our basic constructions may be altered to provide other embodiments that utilize the products and processes of this invention.

We claim:

1. A compound selected from the group consisting of:

I-10
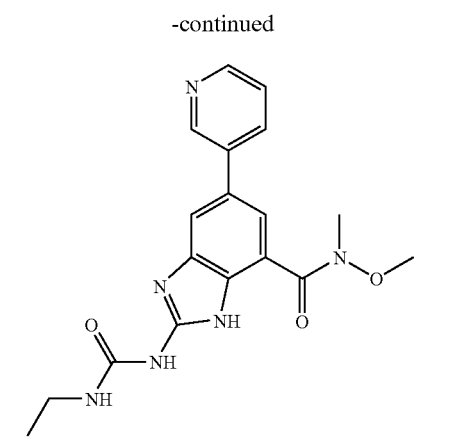
I-11
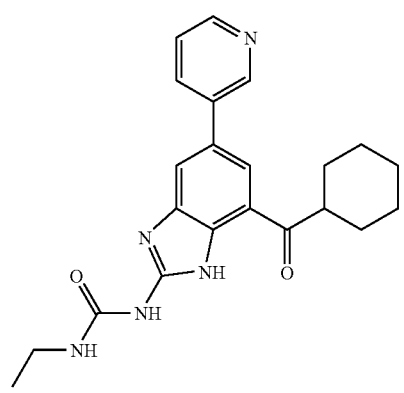
I-12
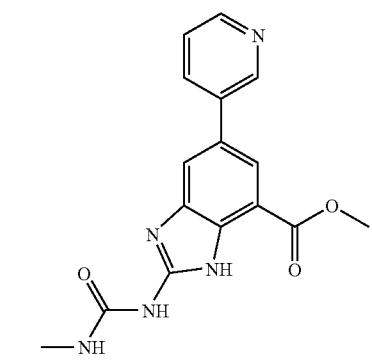
I-15
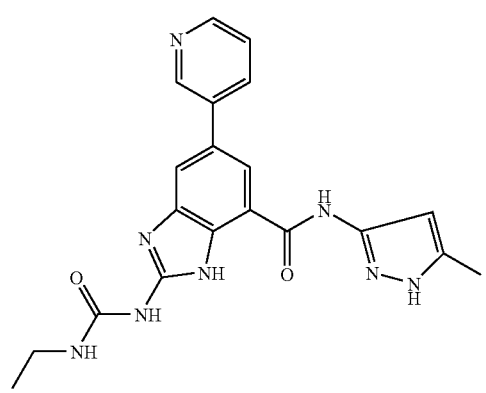
I-17
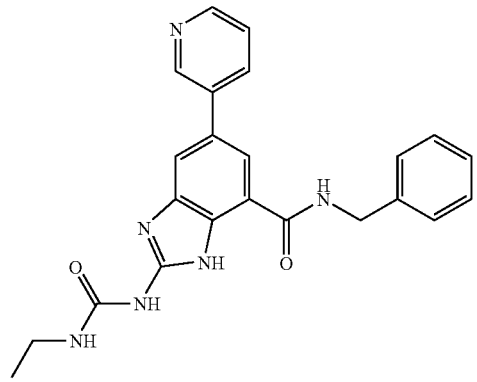
I-18
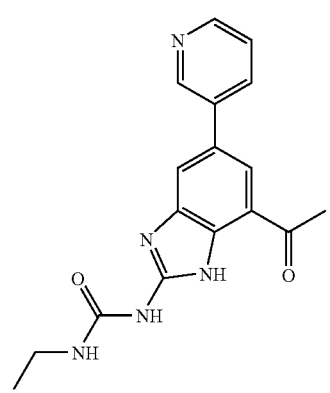
I-19
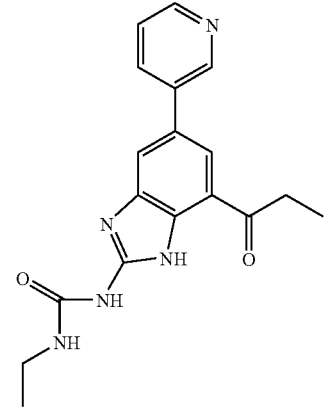
I-20
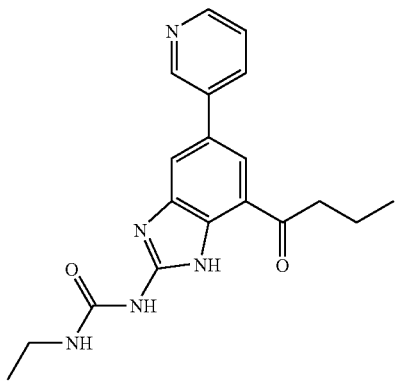

-continued
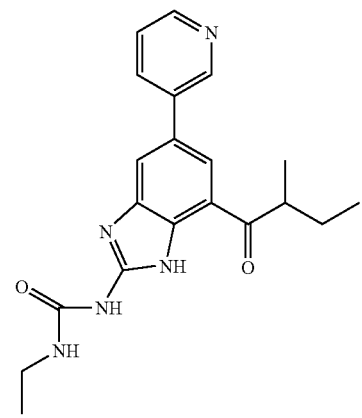
I-21
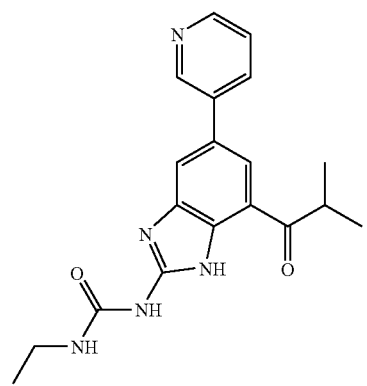
I-22
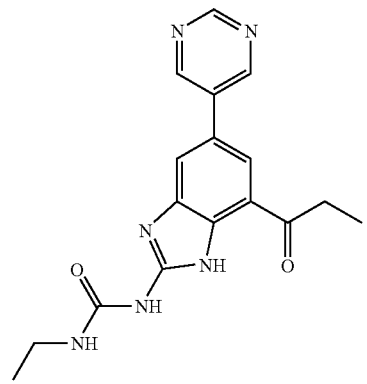
I-23
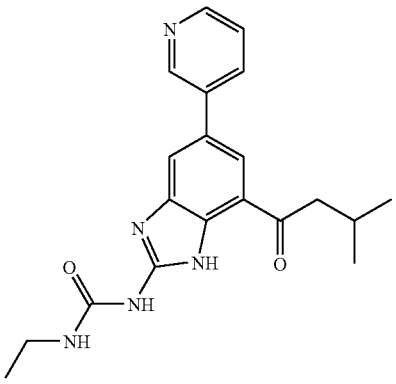
I-24
-continued
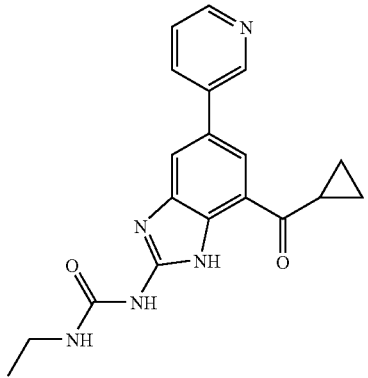
I-25
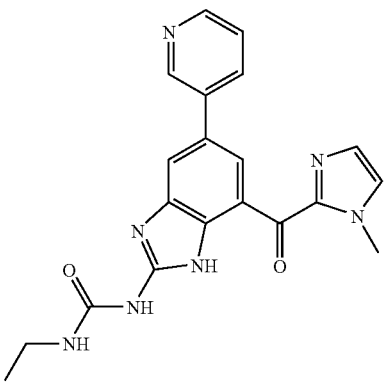
I-26
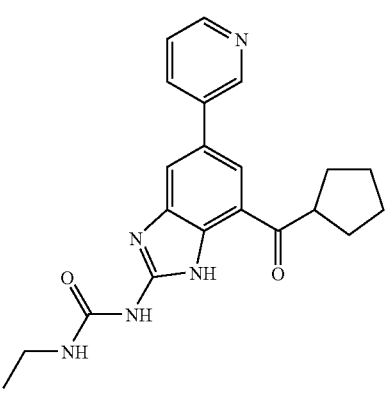
I-28
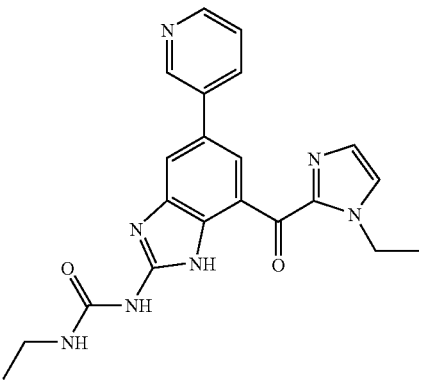
I-29

I-30
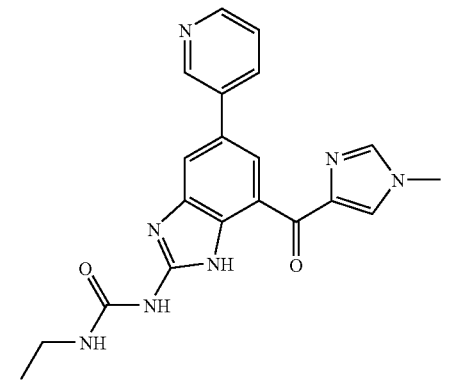
I-31
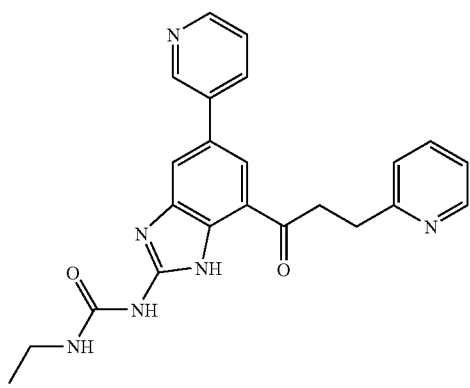
I-32
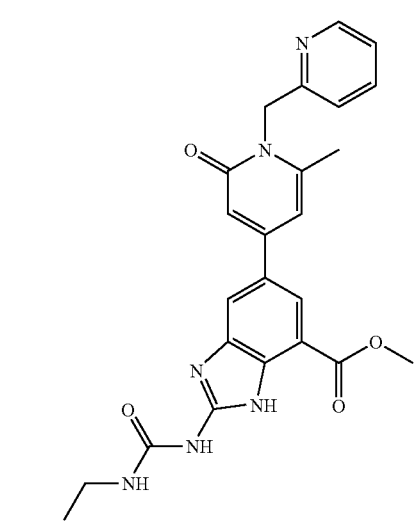
I-33
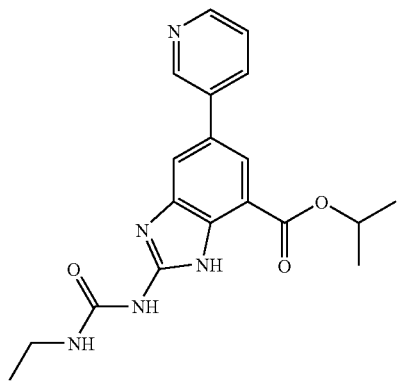
I-34
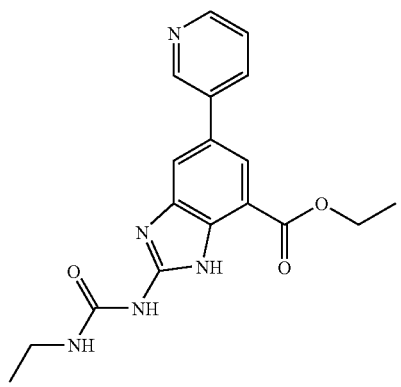
I-35
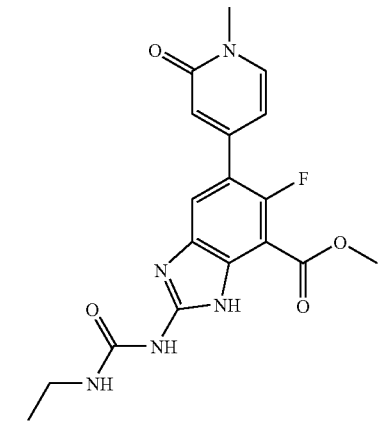
I-36
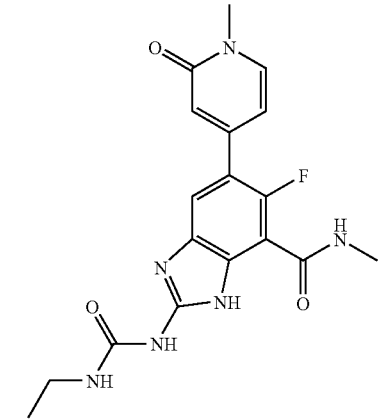

-continued
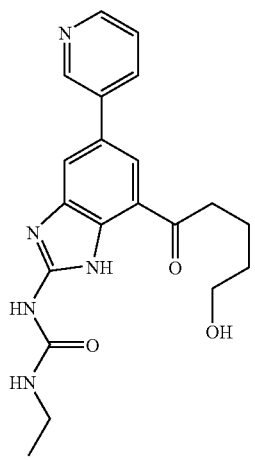
I-37
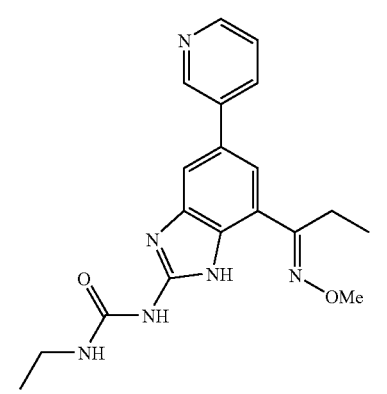
I-38
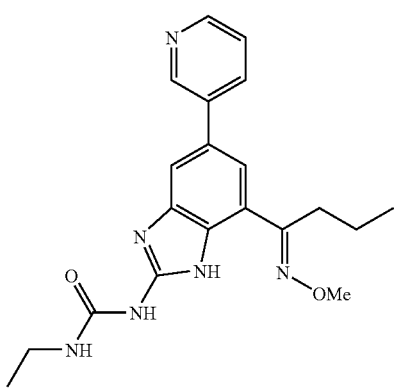
I-39
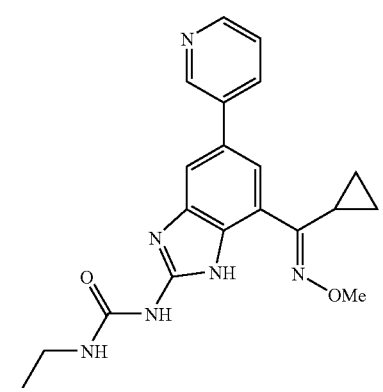
I-40
-continued
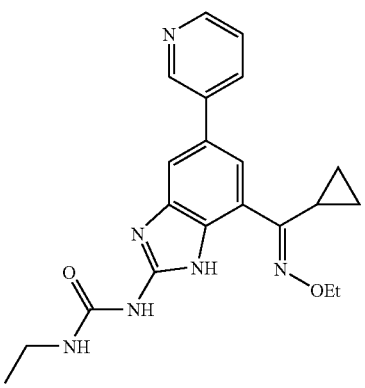
I-41
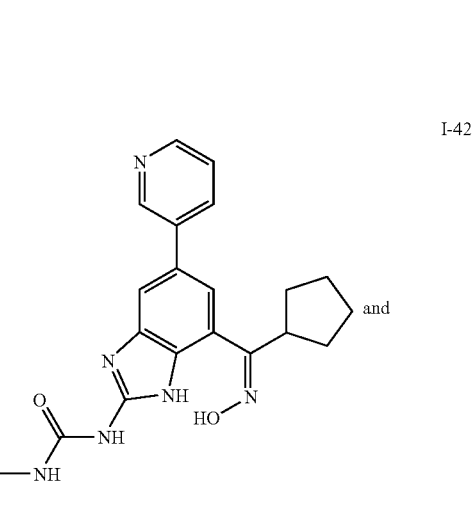
I-42
and
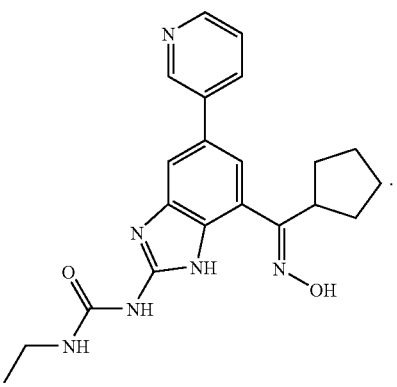
I-43
2. A composition comprising an effective amount of a compound according to claim 1 and a pharmaceutically acceptable carrier, adjuvant, or vehicle.
* * * * *